(12) United States Patent
Correa, Jr. et al.

(10) Patent No.: US 9,200,260 B2
(45) Date of Patent: *Dec. 1, 2015

(54) COMPOSITIONS AND METHODS FOR THE TRANSFER OF A HEXOSAMINE TO A MODIFIED NUCLEOTIDE IN A NUCLEIC ACID

(71) Applicant: New England Biolabs, Inc., Ipswich, MA (US)

(72) Inventors: Ivan R. Correa, Jr., Ipswich, MA (US); Nan Dai, Gloucester, MA (US); Jurate Bitinaite, Rowley, MA (US); Sriharsa Pradhan, Wenham, MA (US); Hang-Gyeong Chin, South Hamilton, MA (US)

(73) Assignee: New England Biolabs, Inc., Ipswich, MA (US)

( * ) Notice: Subject to any disclaimer, the term of this patent is extended or adjusted under 35 U.S.C. 154(b) by 66 days.

This patent is subject to a terminal disclaimer.

(21) Appl. No.: 13/804,804

(22) Filed: Mar. 14, 2013

(65) Prior Publication Data

US 2014/0127677 A1    May 8, 2014

Related U.S. Application Data

(60) Provisional application No. 61/722,968, filed on Nov. 6, 2012, provisional application No. 61/723,427, filed on Nov. 7, 2012, provisional application No. 61/724,041, filed on Nov. 8, 2012, provisional application No. 61/611,295, filed on Mar. 15, 2012.

(51) Int. Cl.
*C12N 9/02* (2006.01)
*C12Q 1/68* (2006.01)
(Continued)

(52) U.S. Cl.
CPC .............. *C12N 9/0069* (2013.01); *C07H 19/06* (2013.01); *C07H 21/00* (2013.01); *C07K 14/47* (2013.01); *C12N 9/1051* (2013.01); *C12N 9/22* (2013.01); *C12P 19/18* (2013.01); *C12P 19/30* (2013.01); *C12P 19/34* (2013.01); *C12Q 1/68* (2013.01); *C12Q 1/683* (2013.01); *C12Q 1/6806* (2013.01);
(Continued)

(58) Field of Classification Search
None
See application file for complete search history.

(56) References Cited

U.S. PATENT DOCUMENTS

| 7,666,612 B2 | 2/2010 | Johnsson et al. |
| 7,799,524 B2 | 9/2010 | Kindermann et al. |

(Continued)

FOREIGN PATENT DOCUMENTS

| WO | WO 02/083937 A2 | 10/2002 |
| WO | WO 2004/072232 A2 | 8/2004 |

(Continued)

OTHER PUBLICATIONS

Endre et al., Metabolism and Interactions: The Chemistry and Biology of Compounds Containing Amino Sugars (vol. 2), 1966, Academic Press Inc., p. 19 only.*

(Continued)

*Primary Examiner* — Alexander Kim
(74) *Attorney, Agent, or Firm* — New England Biolabs, Inc; Harriet M. Strimpel

(57) ABSTRACT

Nucleic acids comprising β-glucosaminyloxy-5-methylcytosine; compositions, kits and methods of producing the nucleic acids using a glycosyltransferase; and methods of using the nucleic acids are described.

7 Claims, 15 Drawing Sheets

(51) Int. Cl.
| | |
|---|---|
| C07H 21/00 | (2006.01) |
| C12P 19/18 | (2006.01) |
| C12P 19/30 | (2006.01) |
| C12P 19/34 | (2006.01) |
| C12N 9/00 | (2006.01) |
| C12N 9/22 | (2006.01) |
| C07K 14/47 | (2006.01) |
| C07H 19/06 | (2006.01) |
| C12N 9/10 | (2006.01) |

(52) U.S. Cl.
CPC ............ *C12Q 1/6809* (2013.01); *C12Q 1/6827* (2013.01); *C07K 2319/80* (2013.01); *C07K 2319/81* (2013.01)

(56) References Cited

U.S. PATENT DOCUMENTS

| | | | |
|---|---|---|---|
| 7,888,090 | B2 | 2/2011 | Barnikow et al. |
| 7,939,284 | B2 | 5/2011 | Johnsson et al. |
| 8,163,479 | B2 | 4/2012 | Jaccard et al. |
| 8,178,314 | B2 | 5/2012 | Kindermann et al. |
| 8,227,602 | B2 | 7/2012 | Gautier et al. |
| 8,367,361 | B2 | 2/2013 | Johnsson et al. |
| 2010/0330645 | A1* | 12/2010 | DeFrees et al. ............... 435/188 |
| 2011/0236894 | A1 | 9/2011 | Rao et al. |

FOREIGN PATENT DOCUMENTS

| | | |
|---|---|---|
| WO | WO 2004/104588 A1 | 12/2004 |
| WO | WO 2006/114409 A1 | 11/2006 |
| WO | WO 2008/012296 A1 | 1/2008 |
| WO | WO 2011/025819 A1 | 3/2011 |
| WO | WO2011091146 | 7/2011 |
| WO | WO2011127136 | 10/2011 |
| WO | WO2014074445 * | 5/2014 |

OTHER PUBLICATIONS

Edited by Reiss et al., Fundamenetal Medical Mycology, 2012, John Wiley & Sons, Inc. Provided one page showing the section of 9.9.2.8.*
P40989 (last viewed on Oct. 30, 2014).*
Shen et al., An Easy Colorimetric Assay for Glycosyltransferases., Biochemistry (Moscow), 2010, vol. 75, pp. 944-950.*
Waymouth medium from Gibco (last viewed on Oct. 30, 2014).*
Takahashi, Dolicyl-Phosphate Beta-Glucosyltransferase (ALG5), Handbook of Glycosyltransferases and Related Genes., (2014), pp. 1649-1655.*
Hoffmeister et al. (Two sequence elements of glycosyltransferase involved in urdamycin biosynthesis are responsible for substrate specificity and enzymatic activity., Chemistry &Biology (2001), vol. 8, pp. 557-567.*
Dai et al., Evaluation of UDP-GlcN Derivatives for Selective Labeling of 5-(Hydroxymethyl)cytosine., ChemBioChem, vol. 14, pp. 2144-2152.*
Song et al., Selective chemical labeling reveals the genome-wide distribution of 5-hydroxymethylcytosine., Nature Biotechnology (2011), vol. 29, pp. 68-72.*
Slonczewski et al., pH homeostasis in *Escherichia coli*: Measurement by 31P nuclear magnetic resonance of methylphsophonate and phosphate., Proc. Natl. Acad. Sci. USA (1981), vol. 78, pp. 6271-6275.*
International Search Report for International Application No. PCT/US2013/068269 dated Jan. 9, 2014.
Li, et al., Chemistry and Biology, 11, 1, 107-119, 2004.
Seto, et al., Eur. J. Biochem, 259, 3, 770-775, 1999.
Song, et al., Bioorganic & Medicinal chemistry Letters, 21, 17, 5075-5077, 2011.
Wanunu, et al., J. Am. Chem. Soc., 133:486-492 (2011).
Los, et al., Methods Mol. Biol., 356:195-208 (2007).
Ehrlich, et al., Biochim Biophys Acta, 395:109-119 (1975).
Kinney, et al., J. Biol. Chem., 286:24685-24693 (2011).
Lariviere, et al., J. Mol. Biol., 330:1077-1086 (2003).
Sletten, et al., Angew Chem Int Ed Engl., 48(38):6974-6998 (2009).
Song, et al., Nat. Biotechnol., 29:68-72 (2011).
Morera, et al., J. Mol Biol. 292(3): 717-730 (1999).
Pompeo, et al., J Biol Chem. 276(6): 3833-3839 (2001).
Robertson, et al., Nucleic Aids Research, 39(8), e55 (2011).
Marchesan, et al., Chem. Commun., 4321-4323 (2008).
Takaya, et al., J. Med. Chem, 48:6054-6065 (2005).
Dulcey, et al.,Tetraherdron, 67: 2013-2017 (2011).
Boeggeman, et al., Annual Conference of the Society for Glycobiology, 20, 1511 (2010).
Tomaschewski, et al., Nucleic Acids Research, 12:7551-7568 (1985).
Szwagierczak, et al., Nucleic Acids Research, 38: e181 (2010).
Wang, et al., Anal Biochem, 290:338-346 (2001).
Skelley, et al., J. Chromatogr A, 1132: 304-309 (2006).
Novatchev, et al., J. Biomed Anal, 28:475-486 (2002).
Dai, et al., Evaluation of UDP-GlcN Derivatives for Selective Labeling of 5-(Hydroxymethyl)cytosine, ChemBioChem 2013, 14, 2144-2152.
Ha, et al., The 1.9 Å crystal structure of *Escherichia coli* MurG, membrane-associated glycosyltransferase involved in peptidoglycan biosynthesis, Protein Science ~2000!, 9:1045-1052.

* cited by examiner

SEQUENCE LISTING

```
<160> NUMBER OF SEQ ID NOS: 2

<210> SEQ ID NO 1
<211> LENGTH: 49
<212> TYPE: DNA
<213> ORGANISM: Unknown
<220> FEATURE:
<223> OTHER INFORMATION: Oligonucleotide
<220> FEATURE:
<221> NAME/KEY: modified_base
<222> LOCATION: (22)..(22)
<223> OTHER INFORMATION: 5-hydroxymethylcytosine

<400> SEQUENCE: 1
ctacacccat cacatttacc tcgagtaaga gttgatagta gagttgaga              49

<210> SEQ ID NO 2
<211> LENGTH: 49
<212> TYPE: DNA
<213> ORGANISM: Unknown
<220> FEATURE:
<223> OTHER INFORMATION: Oligonucleotide

<400> SEQUENCE: 2
gatgtgggta gtgtaaatgg agctcattct caactatcat ctcaactct              49
```

COMPOSITIONS AND METHODS FOR THE TRANSFER OF A HEXOSAMINE TO A MODIFIED NUCLEOTIDE IN A NUCLEIC ACID

REFERENCE TO RELATED APPLICATIONS

This application claims the benefit of each of the following patent applications, the entire disclosures of each of which are hereby incorporated by reference into the present application: U.S. 61/611,295, filed Mar. 15, 2012; U.S. Application No. 61/722,968, filed Nov. 6, 2012; U.S. Application No. 61/723, 427, filed Nov. 7, 2012; and U.S. Application No. 61/724,041, filed Nov. 8, 2012. Also incorporated by reference in their entireties are the following applications filed on the same day as the present application: Ser. No. 13/827,087, "Compositions and Methods for Oxygenation of Nucleic Acids Containing 5-Methylpyrimidine"; Ser. No. 13/826,395, "Mapping Cytosine Modifications"; and Ser. No. 13/827,885, "Methods and Compositions for Discrimination Between Cytosine and Modifications Thereof, and for Methylome Analysis."

BACKGROUND

Modified nucleotides in the genome are associated with epigenetics in general and regulation of transcriptional activation in particular. Detection and/or mapping of modified nucleotides in the genome are important for the understanding of the relationship of phenotype to genotype. Examples of modified nucleotides are 5-hydroxymethylcytosine (5-hmC) and 5-methylated cytosine (5-mC). One approach to detection/mapping of these modified nucleotides is bisulfite sequencing. However, this technique cannot differentiate between the two forms. An alternative approach has been to use T4-β-glucosyltransferase (BGT) to transfer glucose from uridine diphospho-glucose (UDP-Glc) to 5-hmC. The glucose is amenable to chemical derivatization with an azide or thio group (US Published Application No: 2011/0236894 and International Published Application No: WO 2011/02581). Alternative substrates for BGT and other glycosyltransferases would prove useful for enhancing the sensitivity and specificity for 5-hmC and other modified nucleotides analysis as well as for multiplex analysis.

SUMMARY OF THE INVENTION

The present invention is derived, in part, from the discovery that a β-glycosyltransferase can be used to transfer glucosamine to modified nucleotides such as 5-hmC. As far as the inventors are aware, glucosaminated nucleic acids do not exist in nature and their synthesis has now been made possible for the first time using the enzymatic methods described in this application. The ability to introduce site-specific modifications to a nucleic acid permits site-specific labeling of a nucleic acid, such as through the amino group of glucosamine. In conjunction with a restriction enzyme that distinguishes glucosaminated and non-glucosaminated nucleic acids, site-specific modification permits selective control over cleavage of the nucleic acid. Moreover, the methods of the invention can be used to specifically modify 5-hmC residues in a nucleic acid, facilitating their subsequent characterization.

Accordingly, in one aspect, the invention provides a composition (such as an enzyme preparation) or a kit useful for modifying a nucleic acid. The composition or kit includes UDP-glucosamine (UDP-GlcN) and a β-glycosyltransferase, such as BGT. Wild-type and mutant forms of BGT are each useful, as described in Example 1. Thus, if BGT variants are used, the variant may be a fragment retaining enzymatic activity, or may contain amino acid substitutions varying the amino acid sequence, while optionally retaining at least 95% identity, at least 90% identity, at least 85% identity, at least 80% identity, at least 75% identity, or at least 70% identity with wild-type BGT or an active fragment thereof. The glucosamine is optionally a 2-glucosamine or a 6-glucosamine, and can include a label, such as a radioactive label. The composition or kit also typically includes a buffer having a pH between 6 and 8, such as between 6.8 and 7.4, for example. Other components, such as a label or an antibody or other binding moiety with an affinity for glucosamine may also be included. In some embodiments, the composition or kit may include a restriction enzyme capable of cleaving a nucleic acid at a site comprising β-glucosyl-5-hydroxymethylcytosine (β-5 gmC) but not a site comprising β-2-glucosaminyl-5-hydroxymethylcytosine.

The invention also provides methods for labeling a modified nucleotide (such as 5-hmC) in a nucleic acid. The methods include combining the nucleic acid with a composition containing both the UDP-glucosamine and the β-glycosyl transferase under conditions permitting the glucosamine to become covalently attached to the modified nucleotide in the nucleic acid. These conditions generally involve appropriate pH (optionally facilitated by a buffer) and temperature. In some embodiments, the methods further include subsequently reacting the covalently attached glucosamine with a label, such as a radioactive label, a fluorophore, a dye, or an affinity label (such as biotin). Some methods of the invention include enriching, detecting, isolating and/or identifying the position of the glucosamine-attached nucleotide in the nucleic acid.

For example, the invention provide methods for detecting a modified nucleotide in a genome or genomic fragment by combining a nucleic acid having a modified nucleotide with UDP-glucosamine and BGT; permitting the glucosamine to become covalently attached to the modified nucleotide in the nucleic acid; and detecting the modified nucleotide either by labeling the glucosaminated modified nucleotide or by modification-specific enzymatic cleavage using, for example, an enzyme capable of cleaving 5-hmC and 5-gmC, but not glucosamine-containing 5-hmC or labeled glucosamine-containing 5-hmC sites. A genomic fragment is typically at least 100 bases in length, and may be at least 1000 bases; at least 10,000 bases; at least 100,000 bases; at least 1,000,000 bases; or greater in length.

The invention also provides methods for detecting a 5-hmC in a nucleic acid or nucleic acid fragment with a composition containing both the UDP-glucosamine and the β-glycosyltransferase by converting a methylcytosine residue into a hydroxymethylcytosine by means of a chemical oxidizing agent or a cytosine oxygenase enzyme and then permitting the glucosamine to become covalently attached to the oxidized nucleotide.

The invention also provides methods for detecting a 5-hmC in a nucleic acid or nucleic acid fragment with a composition containing both the UDP-glucosamine and the β-glycosyltransferase by converting a formylcytosine or carboxylcytosine residue into a hydroxymethylcytosine by means of a chemical reducing agent, such as sodium borohydride, and then permitting the glucosamine to become covalently attached to the reduced nucleotide.

In another aspect, the invention provides nucleic acids modified to include β-5 gmC residues in which one or more of the hydroxyl groups at the 2- and/or 6-positions of the glucosyl moiety have been replaced with amino groups. The modified β-5 gmC is typically a β-glucosaminyloxy-5-methylcytosine, such as β-2-glucosaminyloxy-5-methylcytosine or β-6-glucosaminyloxy-5-methylcytosine. The nucleic acid may be labeled, such as with a fluorophore, an affinity label, a radioactive label or a dye. In some embodiments, the nucleic acid is a mammalian genome or genome fragment.

The invention also provides methods for labeling such a nucleic acid by reacting it with a label (e.g., a fluorophore, an affinity label, a radioactive label or a dye) at a modified (e.g., a β-glucosaminyloxy-5-methylcytosine). Similarly, the invention provides methods for detecting a modified nucleotide in a nucleic acid, such as a genome or genomic fragment, by labeling the modified nucleotide as described above, and subsequently detecting the presence or absence of the label, where the presence of the label is indicative of the presence of the modified nucleotide.

DETAILED DESCRIPTION OF EMBODIMENTS

Figure 1:
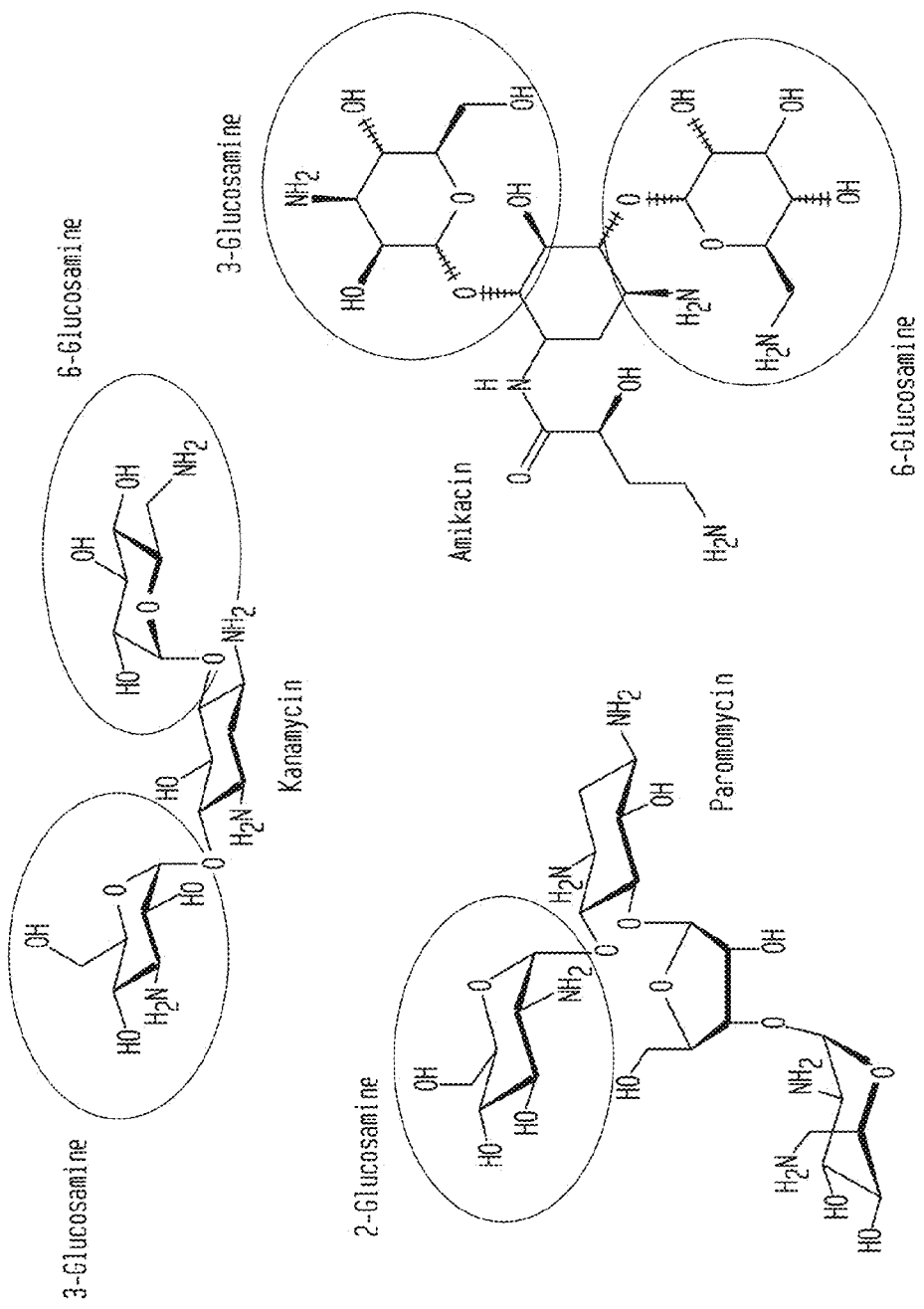
FIG. 1 shows how glucosamines naturally occur in several aminoglycoside antibiotics (e.g., Kanamycin, Paromomycin, Amikacin, etc.) isolated from *Streptomyces* strains.

Certain hexosamines may be used to place a reactive group on a target modified nucleotide in a nucleic acid for the purposes of reacting with a label for sequencing and/or detection. For example, a hydroxyl group, a formyl group or a carbonyl group on a methylated cytosine can be replaced with a GlcN. One of the advantages of using GlcN over glucose cofactors modified with non-naturally occurring groups (e.g., azido-modified sugars) is the availability of various GlcN-modifying enzymes (e.g., Hexokinase, Sigma-Aldrich, St. Louis, Mo.) and GlcN-specific antibodies (e.g., anti-D-GlcN antibody, Abcam PLC, Cambridge, Mass.) that could react or interact with the amine on the glucosaminated cytosine. Fortuitously, the transfer of GlcN to an hmC has been achieved using glucosyltransferases or mutant glucosyltransferases while these enzymes cannot efficiently react with UDP-GlcNAc or UDP-GlcUA.

Exemplary glucosyltransferases are found in bacteriophage, such as T4. The T4 glucosyltransferases show little DNA sequence specificity, suggesting a mechanism of non-specific DNA binding combined with specific 5-hmC recognition.

Variants of the T4 glucosyltransferases can be used. For example, the structure of T4 BGT and the identities of key residues in the enzyme are well understood, facilitating the construction of forms of the protein incorporating one or more amino acid deletions or substitutions. T4 BGT is a monomer comprising 351 amino acid residues and belongs to the α/β protein class. It is composed of two non-identical domains, both similar in topology to Rossmann nucleotide-binding folds, separated by a deep central cleft which forms the UDP-Glc binding site. Amino acids participating in the interaction with UDP include Ile238 (interactions with N3 and O4 of the base); Glu272 (interactions with O2' and O3' of the ribose); Ser189 (interacting with O11 of the α-phosphate); Arg191 (interacting with O12 of the α-phosphate); Arg269 (interacting with 06 of the α-phosphate and O22 of the β-phosphate); and Arg195 (interacting with O21 and O22 of the β-phosphate). Glu22 and Asp100 have been proposed to participate in the catalytic mechanism and other residues have been proposed to be involved in DNA binding or interactions with the UDP-associated sugar (Moréra et al. (1999) "T4 phage beta-glucosyltransferase: substrate binding and proposed catalytic mechanism." *J. Mol. Biol.* 292(3):717-730, the entire disclosure of which is incorporated herein by reference).

Accordingly, a variant glucosyltransferases can be used to add a sugar to a nucleic acid. Variants optionally include an amino acid sequence at least 70% (e.g. at least 75%, at least 80%, at least 82%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%) identical to amino acids 1-351, 10-272 or 22-272 of T4 BGT. As assays for glycosylated nucleic acids (e.g. changes in susceptibility to cleavage by a glycosylation-sensitive endonuclease) are readily available, screening for variants retaining enzymatic activity is relatively straightforward.

2-GlcN is an amino sugar and a prominent precursor in the biochemical synthesis of glycosylated proteins and lipids. 2-GlcN is part of the structure of the polysaccharides chitosan and chitin, which compose the exoskeletons of crustaceans and other arthropods, cell walls in fungi and many higher organisms. 2-GlcN is one of the most abundant monosaccharides. 2-, 3-, 4-, and 6-GlcNs are present in several aminoglycoside antibiotics (e.g., Kanamycin, Paromomycin, Amikacin, etc.) isolated from *Streptomyces* strains (FIG. 1). UDP-GlcN was observed in *E. coli* cells depleted of acetyltransferase activity of GlmU. GlmU catalyzes the last two sequential reactions in the de novo biosynthetic pathway for UDP-GlcNAc, and is responsible for the acetylation of GlcN-1-phosphate (GlcN-1-P) to give GlcNAc-1-P, and for the uridyl transfer from UTP to GlcNAc-1-P which produces UDP-GlcNAc [Pompeo F, Bourne Y, van Heijenoort J, Fassy F, Mengin-Lecreulx D (2001) Dissection of the bifunctional *Escherichia coli* N-acetylglucosamine-1-phosphate uridyltransferase enzyme into autonomously functional domains and evidence that trimerization is absolutely required for glucosamine-1-phosphate acetyltransferase activity and cell growth. J Biol Chem. 276(6), 3833-3839].

Contacting glucosamine-containing 5-hmC with a restriction enzyme or polymerase can be envisioned for sequencing purposes. Nucleic acids containing modified bases that have been GlcN-modified may be sequenced directly in single-molecule real-time (SMRT) DNA sequencing for high-throughput, base-resolution 5-hmC detection using a sequencer provided, for example, by Pacific Biosciences, Menlo Park, Calif. In SMRT DNA sequencing, polymerase kinetic signatures provide the basis for discrimination between the DNA modifications. The polymerase rate at and around the modified base position in the DNA template is slowed compared to unmodified DNA, and this retardation is enhanced when 5-hmC is reacted with GlcN to provide a unique kinetic signature in SMRT DNA sequencing. This signal is more easily detectable than the signal from glycosylated 5-hmC or from 5-hmC and information from this enhanced signal can be used algorithmically to increase the confidence of 5-hmC assignments.

Direct detection of 5-hmC in DNA samples has been achieved by nanopore amperometry [Wanunu M, Cohen-Karni D, Johnson R R, Fields L, Benner J, Peterman N, Zheng Y, Klein M L, Drndic M. (2011) Discrimination of methylcytosine from hydroxymethylcytosine in DNA molecules. J Am Chem. Soc. 133(3), 486-492. In this technique, ion current signatures for DNA molecules threaded through nanopores are associated with the polarity of the cytosine modification. Nucleic acids containing modified bases that have been GlcN-modified may be sequenced directly in nanopore amperometry DNA sequencing for high-throughput, base-resolution 5-hmC detection. Because GlcNs are charged in buffers at and around physiological pH, the modification of 5-hmC with GlcN can provide a unique ion current signature in nanopore amperometry DNA sequencing and this information can be used to increase the confidence of 5-hmC assignments.

Glucosamine-containing 5-hmC residues can be detected using GlcN specific enzymes. For example, GlcN can be phosphorylated by an enzyme hexokinase (HK, EC 2.7.1.1.) and adenosine-5'-triphosphate (ATP) to form GlcN-6-phosphate and adenosine-5'-diphosphate (ADP). Commercially available detection kits for GlcN assay (K-GAMINE; Megazyme International Ireland, Bray, Co. Wicklow, Ireland) consist of enzymatic sequential reactions (hexokinase, glucose-6-phosphate dehydrogenase, phosphoglucose isomerase, and GlcN-6-P deaminase), in which the amount of nicotinamide adenine dinucleotide phosphate (NADPH) formed is stoichiometric with the amount of GlcN. The NADPH is measured by the increase in absorbance at 340 nm. Such kits are suitable for manual, auto-analyser and microplate formats. Once GlcN-containing 5-hmC is converted to GlcN-6-phosphate, various enzymatic-based assays can designed for the detection of 5-hmC, including the use of GlcN-6-phosphate deaminase (EC 3.5.99.6), GlcN-6-phosphate isomerase (EC 3.5.99.6), GlcN-6-phosphate N-acetyltransferase (EC 2.3.1.4), or other enzymes known in the art.

Another example of enzymes that can modify GlcN residues are Heparan-sulfate 6-O-sulfotransferases (HS6ST) (EC 2.8.2.-), UDP-GlcNAc6-O-sulfotransferase (EC=2.8.2.-), and related enzymes known in the art. HS6ST is a 6-O-sulfation enzyme which catalyzes the transfer of sulfate from 3'-phosphoadenosine 5'-phosphosulfate (PAPS) to position 6 of the N-sulfoglucosamine residue (GlcNS) of heparan sulfate. O-sulfotransferase enzymatic-based assays can used for the detection of 5-hmC by or after the conversion of GlcN-containing 5-hmC into GlcN-6-sulfate.

Glucosamine-containing 5-hmC can be detected using radiolabeled UDP-[3H]GlcN, UDP-[14C]GlcN, UDP-[3H, 14C]GlcN, [α-32P]UDP-GlcN or [β-32P]UDP-GlcN, and BGT to generate a radioactive output and/or radioactively labeled GlcN-containing nucleotides which can be subsequently detected directly by scintillation counting.

Glucosamine-containing 5-hmC can provide a target for pull-down by immobilized J-binding protein 1. J-binding proteins from African trypanosomes and related kinetoplastids which specifically bind to DNA containing the J-base (β-glucosyl-5-hydroxymethyluracil) have been shown to cross-react with β-5 gmC containing DNA [Robertson A B, Dahl J A, Vågbø C B, Tripathi P, Krokan H E, Klungland A (2011) A novel method for the efficient and selective identification of 5-hmC in genomic DNA Nucleic Acids Res. 39(8), e55]. Commercially available enrichment kits for the specific enrichment of 5-hmC containing DNA (Quest 5-hmC™ DNA Enrichment Kit; Zymo Research, Irvine, Calif.) featuring J-base binding protein (JBP) consist of converting 5-hmC to 5 gmC using a glycosyltransferase (e.g., BGT), follow by adding JBP immobilized in magnetic beads, and then washing and eluting the enriched 5-hmC containing DNA. It is conceivable that JBP proteins may also bind to other DNA glycosylated forms, including glucosamine-containing 5-hmC.

Glucosamine-containing 5-hmC can be chemically oxidized with sodium periodate, which converts the sugar vicinal hydroxyl groups to aldehydes, and further modified with an aldehyde-reactive probe. An aldehyde-reactive probe can be, for instance, a biotin hydrazide (e.g., Z-Link Hydrazide-Biotin Reagents, Thermo Scientific, Waltham, Mass.) for pull-down and affinity-purification using streptavidin or avidin beads; a fluorophore hydroxylamine (e.g., Alexa Fluor® 488 Hydroxylamine, Life Technologies, Carlsbad, Calif.) or a fluorophore hydrazide (e.g., Alexa Fluor® 647 Hydrazide, Life Technologies, Carlsbad, Calif.) for fluorescence-based detection.

Glucosamine-containing 5-hmC residues can be detected using GlcN specific chemistry. Specific incorporation of GlcN into 5-hmC residues via UDP-GlcN transglycosylation reaction of mediated by BGT permits the labeling of some or all available 5-hmC bases in the acceptor DNA at the GlcN amino functional group. Amino group reactions offer simplicity and versatility to the identification of 5-hmC in DNA samples by means of readily available and inexpensive amino-reactive fluorophores or affinity reagents containing a label L. In one embodiment, the label L can be used for 5-hmC enrichment using an affinity label such as biotin or other binding ligand that can be installed onto GlcN-containing 5-hmC residues via activated ester chemical coupling. In another embodiment, GlcN-containing 5-hmC residues can be directly labeled with detectable probe, such as amine-reactive fluorescent or fluorogenic reagents.

The label L of the substrate can be chosen by those skilled in the art dependent on the application for which the fusion protein is intended. Labels are such that the labeled GlcN-containing nucleotide carrying label L is easily detected or separated from its environment. Other labels considered are those which are capable of sensing and inducing changes in the environment of the labeled GlcN-containing nucleotide or labels which aid in manipulating the GlcN-containing nucleotide by the physical and/or chemical properties of the GlcN substrate specifically introduced into the nucleotide.

The label L is designed to covalently react with the amino group of GlcN-containing nucleotides. Examples of amino-reactive groups are isocyanates, isothiocyanates, active esters (e.g., succinimidyl esters, sulfosuccinimidyl esters, tetrafluorophenyl esters, sulfotetrafluorophenyl esters, sulfodicholorphenol esters), carboxylic acids, acid halides, anhydrides, acyl azides, dichlorotriazines, and sulfonyl chlorides, which form ureas, thioureas, carboxamides, or sulfonamides upon reaction with amines. Other amine-reactive groups are aldehydes, dialdehydes, ketones, vinyl sulfones, vinyl esters, alkyl halides, peroxides, and epoxides.

A label L as understood in the context of the invention is a substituent different from hydrogen or from standard functional groups, in particular different from hydrogen, hydroxy, amino, halogen, carboxylate, carboxamide, carboxylic ester, nitrile, cyanate, isocyanate, sulfonate, sulfonamide, sulfonic ester, aldehyde, ketone, ether, and thioether substituent. Examples of a label include a spectroscopic probe such as a fluorophore or a chromophore, a magnetic probe or a contrast reagent; a radioactively labeled molecule; a molecule which is one part of a specific binding pair which is capable of specifically binding to a partner; a molecule that is suspected to interact with other biomolecules; a library of molecules that are suspected to interact with other biomolecules; a molecule which is capable of crosslinking to other molecules; a molecule which is capable of generating hydroxyl radicals upon exposure to $H_2O_2$ and ascorbate, such as a tethered metal-chelate; a molecule which is capable of generating reactive radicals upon irradiation with light, such as malachite green; a molecule covalently attached to a solid support, where the support may be a glass slide, a microtiter plate or any polymer known to those proficient in the art; a nucleic acid or a derivative thereof capable of undergoing base-pairing with its complementary strand; a lipid or other hydrophobic molecule with membrane-inserting properties; a biomolecule with desirable enzymatic, chemical or physical properties; or a molecule possessing a combination of any of the properties listed above.

Further labels L are positively charged linear or branched polymers which are known to facilitate the transfer of attached molecules over the plasma membrane of living cells. This is of particular importance for substances which otherwise have a low cell membrane permeability or are in effect impermeable for the cell membrane of living cells. A non-cell permeable GlcN-containing nucleotide and/or GlcN substrate will become cell membrane permeable upon conjugation to such a group L. Such cell membrane transport enhancer groups L comprise, for example, a linear poly(arginine) of D- and/or L-arginine with 6-15 arginine residues, linear polymers of 6-15 subunits which each carry a guanidinium group, oligomers or short-length polymers of from 6 to up to 50 subunits, a portion of which have attached guanidinium groups, and/or parts of the sequence of the HIV-tat protein, in particular the subunit Tat49-Tat57 (RKKRRQRRR in the one letter amino acid code).

Some labels L are spectroscopic probes and molecules which are one part of a specific binding pair that is capable of specifically binding to a partner (so-called affinity labels). Also, certain labels L are molecules covalently attached to a solid support. Spectroscopic probes are optionally fluorophores. When the label L is a fluorophore, a chromophore, a magnetic label, a radioactive label or the like, detection is by standard means adapted to the label and whether the method is used in vitro or in vivo. Particular examples of labels L are also radioactively labeled hexosamines.

Optionally, the labels are such that L of one GlcN-containing nucleotide (L1) is one member and L of a another GlcN-containing nucleotide or a differently labeled nucleotide (L2) is the other member of two interacting spectroscopic probes L1/L2, wherein energy can be transferred nonradiatively between the donor and acceptor (another fluorophore or a quencher) when they are in close proximity (less than 10 nanometer distance) through either dynamic or static quenching. An example of such a pair of labels L1/L2 is a FRET (Förster (Fluorescence) resonance energy transfer).

Particular fluorophores considered are: Alexa Fluor dyes, including Alexa Fluor® 350, 405, 430, 488, 514, 532, 546, 555, 568, 594, 610, 633, 647, 660, 680, 700, 750, and 790 (Life Technologies, Carlsbad, Calif.); coumarin dyes, including 3-cyano-7-hydroxycoumarin, 6,8-difluoro-7-hydroxy-4-methylcoumarin, 7-amino-4-methylcoumarin, 7-ethoxy-4-trifluoromethylcoumarin, 7-hydroxy-4-methylcoumarin, 7-hydroxycoumarin-3-carboxylic acid, 7-dimethylaminocoumarin-4-acetic acid, 7-amino-4-methyl-coumarin-3-acetic acid, and 7-diethylamino-coumarin-3-carboxylic acid (Life Technologies, Carlsbad, Calif.); BODIPY® dyes, including BODIPY 493/503, FL, R6G, 530/550, TMR, 558/568, 564/570, 576/589, 581/591, TR, 630/650, and 650/655 (Life Technologies, Carlsbad, Calif.); Quantum Dots, including Qdot® 545 ITK™, Qdot 565 ITK, Qdot 585 ITK, Qdot 605 ITK, Qdot 655 ITK, Qdot 705 ITK, and Qdot 800 ITK (Life Technologies, Carlsbad, Calif.); Oregon Green® dyes, including Oregon Green 488, 488, and 514 (Life Technologies, Carlsbad, Calif.); LanthaScreen® Tb Chelates (Life Technologies, Carlsbad, Calif.); Rhodamine 110, Rhodamine Green, Rhodamine Red, Texas Red-X, Cascade Blue, Pacific Blue, Marina Blue, Pacific Orange, Dapoxyl Sulfonyl Chloride, Dapoxyl Carboxylic Acid, 1-Pyrenebutanoic Acid, 1-Pyrenesulfonyl Chloride, 2-(2,3-Naphthalimino) ethyl Trifluoromethanesulfonate, 2-Dimethylaminonaphthalene-5-Sulfonyl Chloride, 2-Dimethylaminonaphthalene-6-Sulfonyl Chloride, 3-Amino-3-Deoxydigoxigenin Hemisuccinamide, 4-Sulfo-2,3,5,6-Tetrafluorophenol, 5-(and-6)-Carboxyfluorescein, 5-(and-6)-Carboxynaphthofluorescein, 5-(and-6)-Carboxyrhodamine 6G, 5-(and-6)-Carboxytetramethylrhodamine, 5-(and-6)-Carboxy-X-Rhodamine, 5-Dimethylaminonaphthalene-1-Sulfonyl Chloride (Dansyl Chloride), 6-((5-Dimethylaminonaphthalene-1-Sulfonyl)amino) Hexanoic Acid, Succinimidyl Ester (Dansyl-X, SE), Lissamine Rhodamine B Sulfonyl Chloride, Malachite Green isothiocyanate, NBD Chloride, 4-Chloro-7-Nitrobenz-2-Oxa-1,3-Diazole (4-Chloro-7-Nitrobenzofurazan), NBD Fluoride; 4-Fluoro-7-Nitrobenzofurazan, 4-Fluoro-7-Nitrobenz-2-Oxa-1,3-Diazole, NBD-X, and PyMPO (Life Technologies, Carlsbad, Calif.); CyDyes®, including Cy 3, Cy 3B, Cy 3.5, Cy 5, Cy 5.5, Cy 7 (GE Healthcare, Little Chalfont, UK); ATTO dyes, including ATTO 390, 425, 465, 488, 495, 520, 532, 550, 565, 590, 594, 610, 611X, 620, 633, 635, 637, 647, 647N, 655, 680, 700, 729, and 740 (ATTO-TEC GmbH, Siegen, Germany); DY dyes, including DY 350, 405, 415, 490, 495, 505, 530, 547, 548, 549, 550, 554, 555, 556, 560, 590, 591, 594, 605, 610, 615, 630, 631, 632, 633, 634, 635, 636, 647, 648, 649, 650, 651, 652, 654, 675, 676, 677, 678, 679, 680, 681, 682, 700, 701, 703, 704, 730, 731, 732, 734, 749, 750, 751, 752, 754, 776, 777, 778, 780, 781, 782, 800, 831, 480XL, 481XL, 485XL, 510XL, 520XL, and 521XL (Dyomics, Jena, Germany); CF™ dyes, including CF 350, 405, 485, 488, 532, 543, 555, 568, 594, 620R, 633, 640R, 647, 660C, 660R, 680, 680R, 750, 770, and 790 (Biotium, Hayward, Calif.); CAL Fluor® dyes, including CAL Fluor Gold 540, Orange 560, Red 590, Red 610, Red 635 (Biosearch Technologies, Novato, Calif.); Quasar® dyes, including Quasar 570, 670, 705 (Biosearch Technologies, Novato, Calif.); Biosearch Blue and Pulsar® 650 (Biosearch Technologies, Novato, Calif.); DyLight® Fluor dyes, including DYLight 350, 405, 488, 550, 594, 633, 650, 680, 755, 800 (Thermo Fisher Scientific, Waltham, Mass.); FluoProbes® dyes, including FluoProbes 390, 488, 532, 547H, 594, 647H, 682, 752, 782 (Interchim, Montluçon Cedex, France); SeTau dyes, including SeTau 380, 425, 405, 404, 655, 665, and 647 (SETA BioMedicals, Urbana, Ill.); Square dyes, including Square 635, 660, and 685 (SETA BioMedicals, Urbana, Ill.); Seta dyes, including, Seta 470, 555, 632, 633, 646, 650, 660, 670, 680, and 750 (SETA BioMedicals, Urbana, Ill.); SQ-565 and SQ-780 (SETA BioMedicals, Urbana, Ill.); Chromeo™ dyes, including Chromeo 488, 494, 505, 546, and 642 (Active Motif, Carlsbad, Calif.); Abberior STAR dyes, including STAR 440SX, 470SX, 488, 512, 580, 635, and 635P (Abberior GmbH, Göttingen, Germany); Abberior CAGE dyes, including CAGE 500, 532, 552, and 590 (Abberior GmbH, Göttingen, Germany); Abberior FLIP 565 (Abberior GmbH, Göttingen, Germany); IRDye® Infrared Dye, including IRDye 650, 680LT, 680RD, 700DX, 750, 800CW, and 800RS (LI-COR Biosciences, Lincoln, Nebr.); Tide Fluor™ dyes, including TF1, TF2, TF3, TF4, TF5, TF6, TF7, and TF8 (AAT Bioquest, Inc., Sunnyvale, Calif.); iFluor™ dyes, including iFluor™ 350, 405, 488, 514, 532, 555, 594, 610, 633, 647, 680, 700, 750, and 790 (AAT Bioquest, Inc., Sunnyvale, Calif.); mFluor™ dyes, including mFluor Blue 570, Green 620, Red 700, Red780, Violet 450, Violet 510, Violet 540, and Yellow 630 (AAT Bioquest, Inc., Sunnyvale, Calif.); trFluor™ Eu and trFluor Tb (AAT Bioquest, Inc., Sunnyvale, Calif.); HiLyte Fluor™ dyes, including HiLyte Fluor 405, 488, 555, 594, 647, 680, and 750 (AnaSpec, Inc., Fremont, Calif.); Terbium Cryptate and Europium Cryptate (Cisbio Bioassays, Codolet, France); and other nucleotide classical dyes, including FAM, TET, JOE, VIC™, HEX, NED, TAMRA, ROX™, Texas Red® (Biosearch Technologies, Novato, Calif.).

Particular quenchers considered are: QSY 35, QSY 9, QSY 7, and QSY 21 (Life Technologies Corporation, Carlsbad, Calif.); Black Hole Quencher®, including BHQ-0, BHQ-1, BHQ-2, and BHQ-3 (Biosearch Technologies, Inc., Novato, Calif.); ATTO 540Q, ATTO 580Q, and ATTO 612Q (ATTO-TEC GmbH, Siegen, Germany); 4-dimethylamino-zobenzene-4'-sulfonyl derivatives (Dabsyl), 4-dimethylaminoazobenzene-4'-carbonyl derivatives (Dabcyl), DNP and DNP-X [6-(2,4-Dinitrophenyl)aminohexanoic acid] (AAT Bioquest, Inc., Sunnyvale, Calif. 94085, USA); DYQ quenchers, including DYQ 425, 505, 1, 2, 660, 661, 3, 700, 4 (Dyomics, Jena, Germany); IRDye® QC-1 (LI-COR Biosciences, Lincoln, Nebr.); Tide Quencher™, including TQ1, TQ2, TQ3, TQ4, TQ5, TQ6, and TQ7 (AAT Bioquest, Inc., Sunnyvale, Calif.); QXL® quenchers, including QXL 490, 570, 610, 670, and 680 (AnaSpec, Inc., Fremont, Calif.); BlackBerry® Quenchers, including BBQ-650 (Berry & Associates, Inc., Dexter, Mich.).

Other labels L are nonfluorescent but form fluorescent conjugates stoichiometrically with amines. These reagents are particularly useful for detecting and quantitating amine-containing nucleotides. Examples of such labels are fluorescamine, aromatic dialdehydes (e.g., o-phthaldialdehyde (OPA) and naphthalene-2,3-dicarboxaldehyde (NDA)), ATTO-TAG CBQCA, ATTO-TAG FQ, 7-nitrobenz-2-Oxa-1, 3-Diazole (NBD) derivatives, dansyl chloride, 1-pyrenesulfonyl chloride, dapoxyl sulfonyl chloride, coumarins, pyrenes, and N-methylisatoic anhydride (Life Technologies Corporation, Carlsbad, Calif.).

Depending on the properties of the label L, the GlcN-containing nucleotide may be bound to a solid support on reaction with the GlcN moiety. The label L may already be attached to a solid support when entering into reaction with GlcN, or may subsequently, i.e. after GlcN is transferred to the nucleotide, be used to attach the labeled GlcN-containing nucleotide to a solid support. The label L may be one member of a specific binding pair, the other member of which is attached or attachable to the solid support, either covalently or by any other means. A specific binding pair considered is e.g. biotin and avidin or streptavidin. Either member of the binding pair may be the label L of the substrate, the other being attached to the solid support. Examples of specific binding pairs allowing covalent binding to a solid support are e.g. SNAP-tag/AGT and benzylguanine derivatives (U.S. Pat. Nos. 7,939,284; 8,367,361; 7,799,524; 7,888,090; and 8,163, 479) or pyrimidine derivatives (U.S. Pat. No. 8,178,314), CLIP-tag/ACT and benzylcytosine derivatives (U.S. Pat. No. 8,227,602), Halotag and chloroalkene derivatives (Los, et al. *Methods Mol Biol.*, 356:195-208 (2007)), serine-beta-lactamases and beta-lactam derivatives (International Patent Application Publication No. WO 2004/072232). Further examples of specific binding pairs allowing covalent binding to a solid support are acyl carrier proteins and modifications thereof (binder proteins), which are coupled to a phosphopantheteine subunit from Coenzyme A (binder substrate) by a synthase protein (U.S. Pat. No. 7,666,612). Examples of labels allowing convenient binding to a solid support are e.g. chitin binding domain (CBD), maltose binding protein (MBP), glycoproteins, transglutaminases, dihydrofolate reductases, glutathione-S-transferase al (GST), FLAG tags, His-tags, or reactive substituents allowing chemoselective reaction between such substituent with a complementary functional group on the surface of the solid support. Examples of such pairs of reactive substituents and complementary functional group are e.g. amine and activated carboxy group forming an amide, azide and a propiolic acid derivative undergoing a 1,3-dipolar cycloaddition reaction, amine and another amine functional group reacting with an added bifunctional linker reagent of the type of activated bis-dicarboxylic acid derivative giving rise to two amide bonds, or other combinations known in the art. Examples of a convenient solid support are e.g. glass surfaces such as glass slides, microtiter plates, and suitable sensor elements, in particular functionalized polymers (e.g. in the form of beads), chemically modified oxidic surfaces, e.g. silicon dioxide, tantalum pentoxide or titanium dioxide, or also chemically modified metal surfaces, e.g. noble metal surfaces such as gold or silver surfaces.

When the label L is capable of generating reactive radicals, such as hydroxyl radicals, upon exposure to an external stimulus, the generated radicals can then inactivate proteins that are in close proximity of the GlcN-containing nucleotide, allowing studying the role of these proteins. Examples of such labels are tethered metal-chelate complexes that produce hydroxyl radicals upon exposure to $H_2O_2$ and ascorbate, and chromophores such as malachite green that produce hydroxyl radicals upon laser irradiation. The use of chromophores and lasers to generate hydroxyl radicals is also known in the art as chromophore assisted laser induced inactivation (CALI). Furthermore, proteins which are in close proximity of the GlcN-containing nucleotide can be identified as such by either detecting fragments of that protein by a specific antibody, by the disappearance of those proteins on a high-resolution 2D-electrophoresis gels or by identification of the cleaved protein fragments via separation and sequencing techniques such as mass spectrometry or protein sequencing by N-terminal degradation.

When the label L is a molecule that can cross-link to other nucleic acids or proteins, e.g. a molecule containing functional groups such as maleimides, active esters, or azides and others known to those proficient in the art, contacting such a labeled GlcN-containing nucleotide that interacts with other nucleic acids or proteins leads to the covalent cross-linking of the GlcN-containing nucleotide with its interacting nucleic acid or protein via the label. This allows the identification of the nucleic acid or protein interacting with the GlcN-containing nucleotide. In a special aspect of cross-linking, the label L is a molecule which enables photo-reactive (light-activated) chemical crosslinking. Labels L for photo cross-linking are e.g. benzophenones, phenyl azides, and diazirines.

Other labels L considered are for example fullerenes, boranes for neutron capture treatment, nucleotides or oligonucleotides, e.g. for self-addressing chips, peptide nucleic acids, and metal chelates, e.g. platinum chelates that bind specifically to DNA. A particular biomolecule with desirable enzymatic, chemical or physical properties is methotrexate. Methotrexate is a tight-binding inhibitor of the enzyme dihydrofolate reductase (DHFR) and can be used with the well-known class of so-called "chemical inducers of dimerization" (CIDs).

All references cited herein are incorporated by reference.

EXAMPLES

Example 1

Evaluation of UDP-GlcN and UDP-Glc Derivatives for Selective Labeling of 5-hmC

Materials and Methods
Enzymes, UDP-GlcN and UDP-Glc Derivatives, and DNA Preparation.

General procedures and reagents for the synthesis of UDP-GlcN and UDP-Glc derivatives are provided in Example 2. The BGT, BGT/Y261L, and AGT, and the restriction endonucleases MfeI, XhoI, and TaqI were obtained from New England Biolabs, Inc. (Ipswich, Mass.). BGT DNA was purified following the protocol adapted from Ehrlich et al. [Ehrlich, M., Ehrlich, K. and Mayo, J. A. (1975) Unusual properties of the DNA from *Xanthomonas* phage XP-12 in which 5-methylcytosine completely replaces cytosine. *Biochim Biophys Acta*, 395, 109-119]. Fluorescein (FAM) labeled double stranded oligonucleotides containing a single 5-hmC residue were synthesized as described by Kinney et al. [Kinney, S. M., Chin, H. G., Vaisvila, R., Bitinaite, J., Zheng, Y., Esteve, P. O., Feng, S., Stroud, H., Jacobsen, S. E. and Pradhan, S. (2011) Tissue-specific distribution and dynamic changes of 5-hmC in mammalian genomes. *J Bio Chem*, 286, 24685-24693]. The final 49-bp ds oligonucleotide sequence is as follows: top strand -5'-/FAM/-CTACACCCATCACATTTAC CT$^{5hm}$CGAGTAAGAGTTGATAGTAGAGTTGAGA-3' (SEQ ID NO:1); and bottom strand -3'-GATGTGGGTAGT-GTAAATGGAGCTCATTCTCAACTATCATCTCAACTC-T-/FAM/-5' (SEQ ID NO:2); (XhoI/TaqI site is underlined).

Glycosylation of BGT DNA with Wild-Type AGT, Wild-Type BGT, and BGT/Y261L in the Presence of UDP-GlcN and UDP-Glc Derivatives.

5-hmC residues were glycosylated by incubating 0.25 μg BGT DNA substrate with 100 ng of wild-type AGT, wild-type BGT, or BGT/Y261L for 1 h at 37° C. in 15 μL reaction containing 1× NEBuffer 4 supplemented with various concentrations of UDP-Glc derivatives (ranging from 1.0 μM to 5.0 mM). After glycosylation, the glucosyltransferase was heat-inactivated by incubating for 10 minutes at 70° C. To analyze the enzyme-catalyzed transfer efficiency, samples were incubated with 1 μL (20 units) MfeI for 1 hour at 37° C. Reaction products were separated by agarose gel electrophoresis and stained with ethidium bromide to check for complete protection of BGT DNA against MfeI cleavage.

Inhibitory Tests of Wild-Type BGT and BGT/Y261L with UDP-2-Azido-Glc.

0.25 μg BGT DNA was combined with various concentrations of UDP-2-Azido-Glc 2 (from 0.02 to 10.0 mM) in the presence of 40 μM native UDP-Glc cofactor (New England Biolabs, Ipswich, Mass.), or combined with various concentrations of natural UDP-Glc (from 0.02 to 20.0 mM) in the presence of 5 mM UDP-2-Azido-Glc 2. After adding 100 ng of wild-type BGT or BGT/Y261L, the reaction mixtures were incubated at 37° C. for 1 hour in 1× NEBuffer 4. After glycosylation, the glucosyltransferase was heat-inactivated by incubating for 10 minutes at 70° C. To analyze the inhibitory effect of UDP-2-Azido-Glc 2, samples were incubated with 1 μL (20 units) MfeI for 1 hour at 37° C. Reaction products were separated by electrophoresis on agarose gel and stained with ethidium bromide.

Glycosylation of 5-hmC-Containing Synthetic Oligonucleotides.

Figure 9:
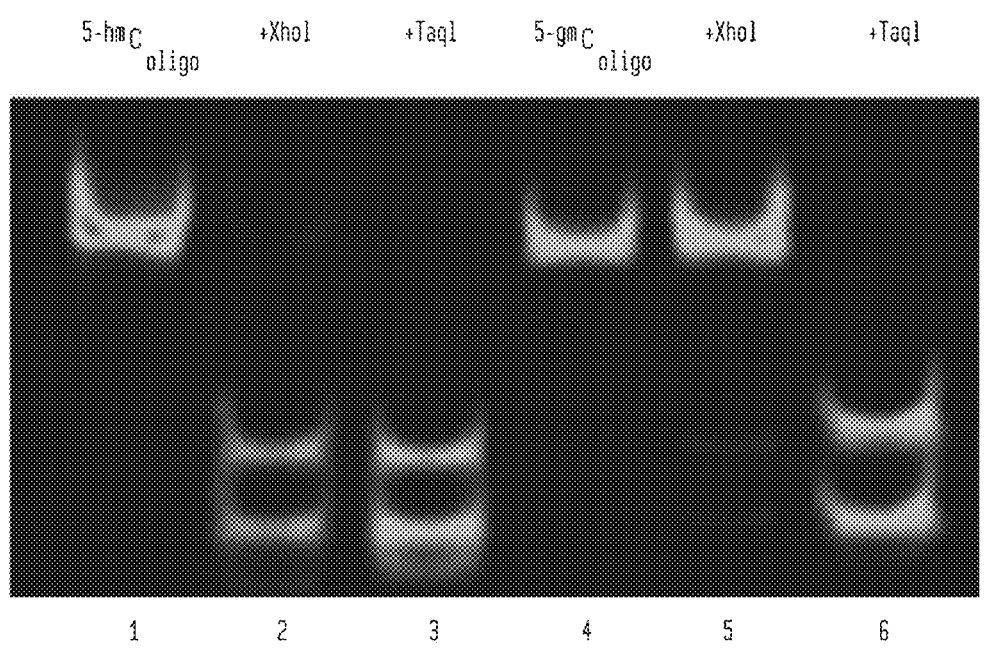
FIG. 9 shows an image of an agarose gel depicting the results of restriction endonuclease cleavage of 5-hmC- and β-5 gmC-containing oligonucleotides.

5-hmC residues were glycosylated by incubating 1 nmol of a 49-bp FAM-labeled double-stranded oligonucleotide substrate with 1 μg of BGT for 18 hours at 37° C. in a total 100 μL reaction containing 50 mM HEPES buffer pH 7.6, 10 mM MgCl$_2$, 50 mM NaCl and supplemented with 0.5 mM modified UDP-glucose derivative. After glycosylation, the oligonucleotide was purified by phenol-chloroform extraction and ethanol precipitation and dissolved in 50 μL H$_2$O. To ensure complete 5-hmC glycosylation, a 10 pmol aliquot was digested with either 1 μL (20 units) of XhoI or TaqI restriction endonuclease for 1 hour at 37° C. For instance, XhoI cuts 5-hmC residues, but does not cut 5-gmC residues resulting from incubation with UDP-6-GlcN; TaqI cuts both 5-hmC and 5-gmC residues (FIG. 9). Reaction products were separated by electrophoresis under non-denaturing conditions on a 10-20% acrylamide gel and visualized using a Typhoon™ 9400 imager (GE Healthcare, Life Sciences, Piscataway, N.J.) with a standard fluorescein filter set (488/526 nm excitation/emission).

Click Chemistry Labeling.

50 pmol of a 6-Azido-Glc-containing 49-bp FAM-labeled oligonucleotide was incubated with the indicated concentrations of dibenzylcyclooctyne-tetramethylrhodamine (DBCO-Fluor 545, Click Chemistry Tools, Scottsdale, Ariz.) in a total 10 μL reaction for 18 hours at room temperature or for 8 hours at 37° C. Unincorporated fluorophore was removed by gel-filtration on a microspin G-50 column. To analyze the labeling efficiency, 10 pmol samples were separated by electrophoresis under non-denaturing conditions on a 10%-20% acrylamide gel and visualized using a Typhoon 9400 imager with standard fluorescein (488/526 nm excitation/emission) and rhodamine (532/580 nm excitation/emission) filter sets.

Activated Ester Labeling.

50 pmol of 2- or 6-GlcN-containing 49-bp FAM-labeled oligonucleotides were incubated with the indicated concentrations of 5-(and-6)-carboxytetramethylrhodamine succinimidyl ester (TAMRA NHS ester, Life Technologies, Carlsbad, Calif.) in 50 mM HEPES buffer pH 7.6 in a total 10 µL reaction at room temperature for 18 hours. Unincorporated fluorophore was removed by gel-filtration on a microspin G-50 column. Electrophoresis was performed on a 10-20% acrylamide gel to check the labeling efficiency. To optimize the coupling conditions, 50 pmol of 6-GlcN-containing 49-bp FAM-labeled oligonucleotide was incubated with 5.0 mM TAMRA NHS ester in different buffers ranging from pH 5.5 to 8.4 as indicated. Unincorporated fluorophore was removed by gel-filtration on a microspin G-50 column. To analyze the labeling efficiency, a 10 pmol aliquot was digested with 1 µL (20 units) TaqI restriction endonuclease for 1 hour at 37° C. Reaction products were separated by electrophoresis under non-denaturing conditions on a 10%-20% acrylamide gel and visualized using a Typhoon 9400 imager with standard fluorescein (488/526 nm excitation/emission) and rhodamine (532/580 nm excitation/emission) filter sets.

Results

Synthesis of UDP-GlcN and UDP-Glc Derivatives.

Figure 2:
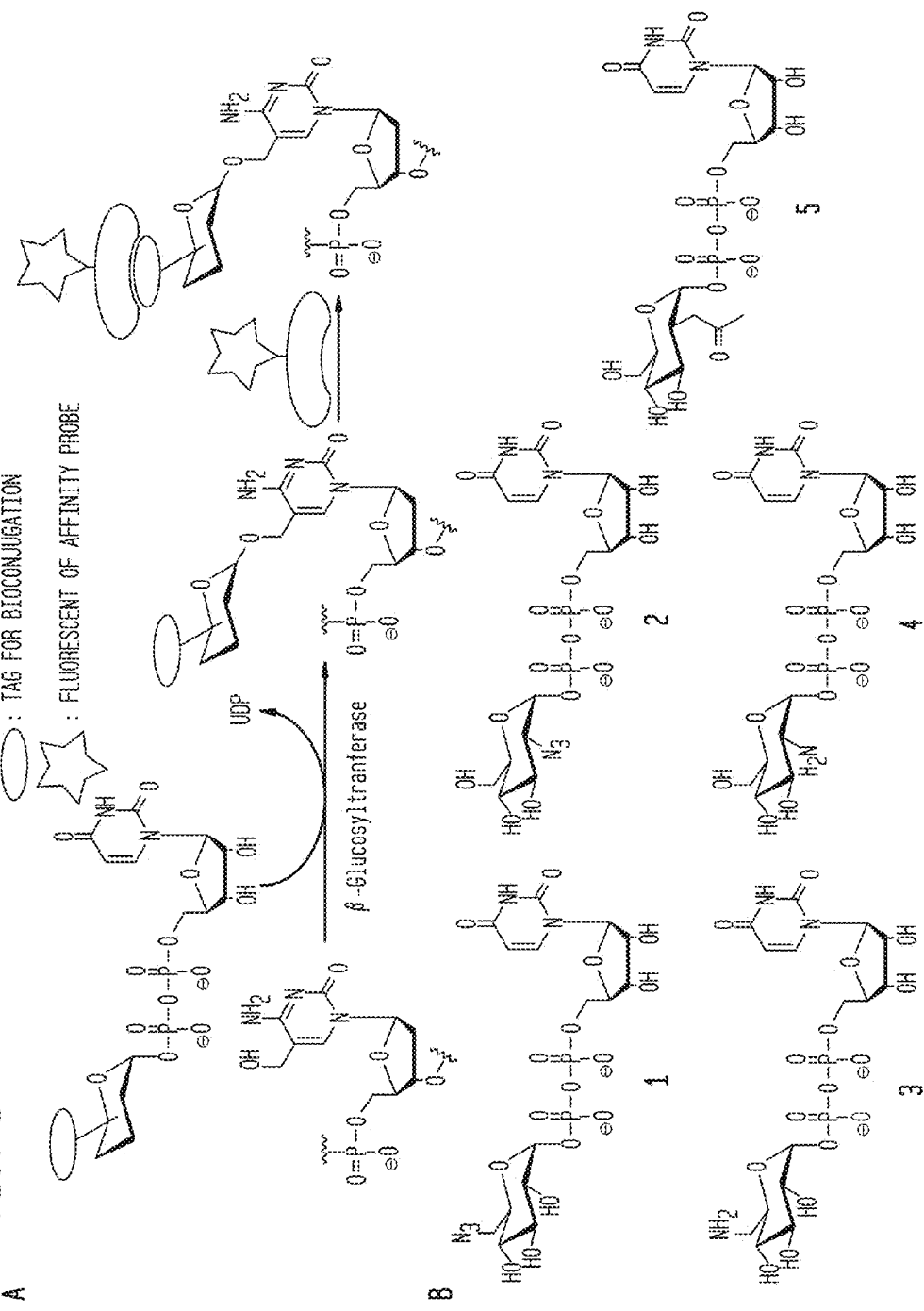
FIG. 2 shows (A) a detection scheme for 5-hmC in DNA using functionalized UDP-Glc derivatives and (B) chemical structures of synthetic UDP-Glc derivatives whose syntheses are described in Example 2.

Referring now to FIG. 2, BGT can be used to add a glucosamine or a modified glucose derivative to the hydroxyl group of 5-hmC using a UDP-Glc derivative as a substrate (FIG. 2A). The available X-ray crystal structure of UDP-Glc/wild-type BGT complex [Lariviere, L., Gueguen-Chaignon, V. and Morera, S. (2003) Crystal structures of the T4 phage beta-glucosyltransferase and the D100A mutant in complex with UDP-glucose: glucose binding and identification of the catalytic base for a direct displacement mechanism. *J. Mol. Biol.*, 330, 1077-1086] shows that the more conservative O3' and O4' hydroxyl groups of UDP-Glc participate in multiple hydrogen bonds within the binding pocket of the enzyme, while O2' and O6' hydroxyl groups are only involved in one hydrogen bond each. Accordingly, it was postulated O2' and O6' hydroxyl would be the most suitable positions for the installation of chemical tags (e.g., including, but not limited to, azido, amino, or ketone) for detection and enrichment of 5-hmC residues in double-stranded DNA (FIG. 2A). Azido, amino, and ketone functional groups have been widely used for in vitro conjugation of large biomolecules under physiological conditions [Sletten, E. M. and Bertozzi, C. R. (2009) Bioorthogonal chemistry: fishing for selectivity in a sea of functionality. *Angew Chem Int Ed Engl*, 48, 6974-6998]. Azido groups can orthogonally react with alkyne functionalized probes via Huisgen-Sharpless azide-alkyne [3+2] (also known as click chemistry) or strain-promoted cycloaddition. Amino groups can specifically react with active esters, such as tetrafluorophenyl (TFP) and N-hydroxysuccinimidyl (NHS) esters. Ketone groups can be selectively modified with hydrazine or hydroxylamino nucleophiles.

The UDP-glucose derivative UDP-6-Azido-Glc 1 was previously demonstrated to be a substrate for the wild-type BGT, showing about a 6-fold decrease in the reaction rate compared to the native UDP-Glc cofactor [Song, C. X., Szulwach, K. E., Fu, Y., Dai, Q., Yi, C., Li, X., Li, Y., Chen, C. H., Zhang, W., Jian, X. et al. (2011) Selective chemical labeling reveals the genome-wide distribution of 5-hydroxymethylcytosine. *Nat. Biotechnol.*, 29, 68-72]. Thus, UDP-6-Azido-Glc 1 was used as a comparative model in these studies. UDP-2-Azido-Glc 2 was synthesized using a similar protocol [Song, C. X., Szulwach, K. E., Fu, Y., Dai, Q., Yi, C., Li, X., Li, Y., Chen, C. H., Zhang, W., Jian, X. et al. (2011) Selective chemical labeling reveals the genome-wide distribution of 5-hydroxymethylcytosine. *Nat. Biotechnol.*, 29, 68-72; Marchesan, S, and Macmillan, D. (2008) Chemoenzymatic synthesis of GDP-azidodeoxymannoses: non-radioactive probes for mannosyltransferase activity. *Chem. Commun.*, 4321-4323].

Figure 3A:
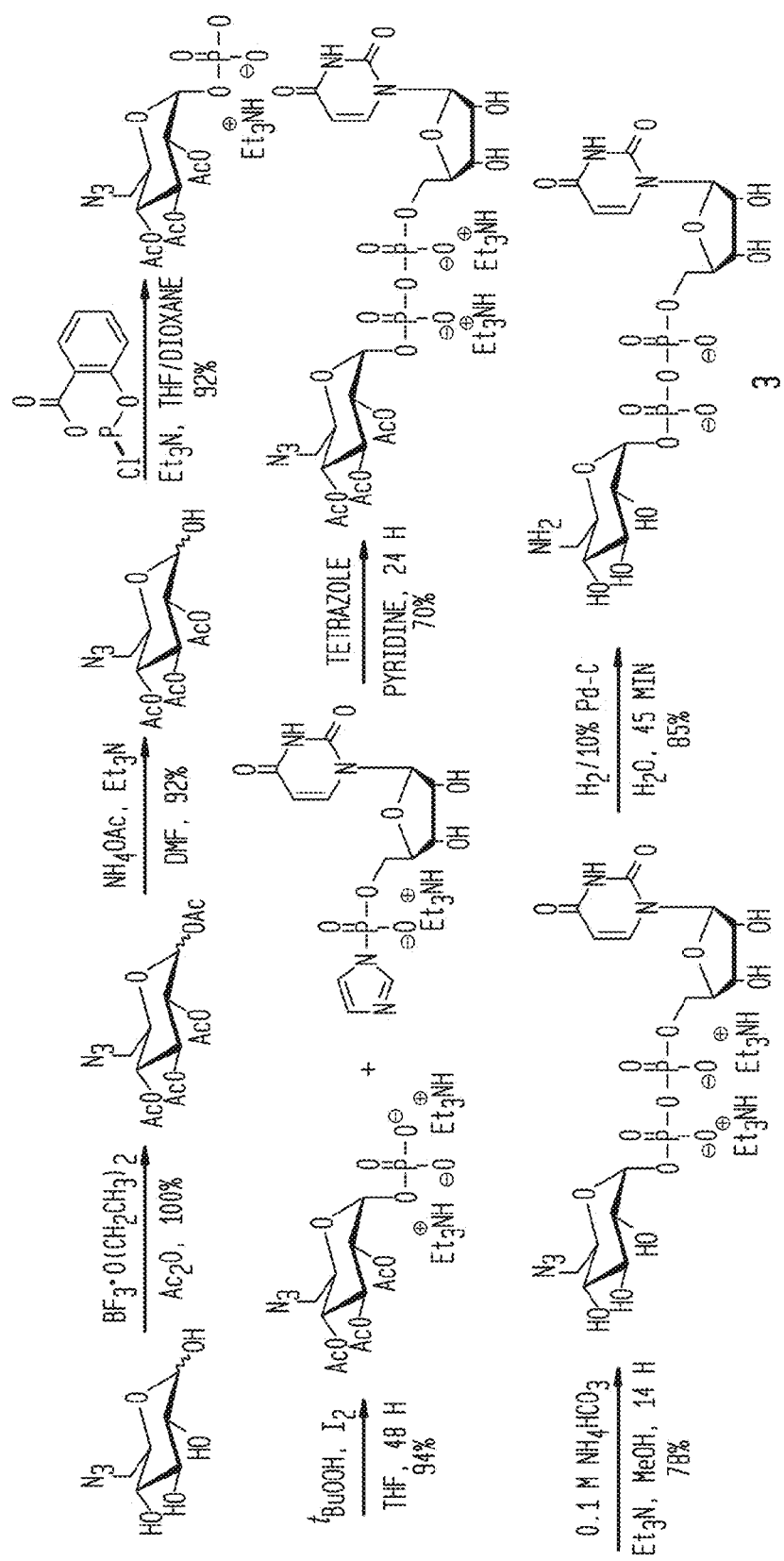
FIG. 3 shows a synthetic scheme for preparing UDP-6-glucosamine (UDP-6-GlcN) 3 (A) and UDP-2-glucosamine (UDP-2-GlcN) 4 (B).
Figure 3B:
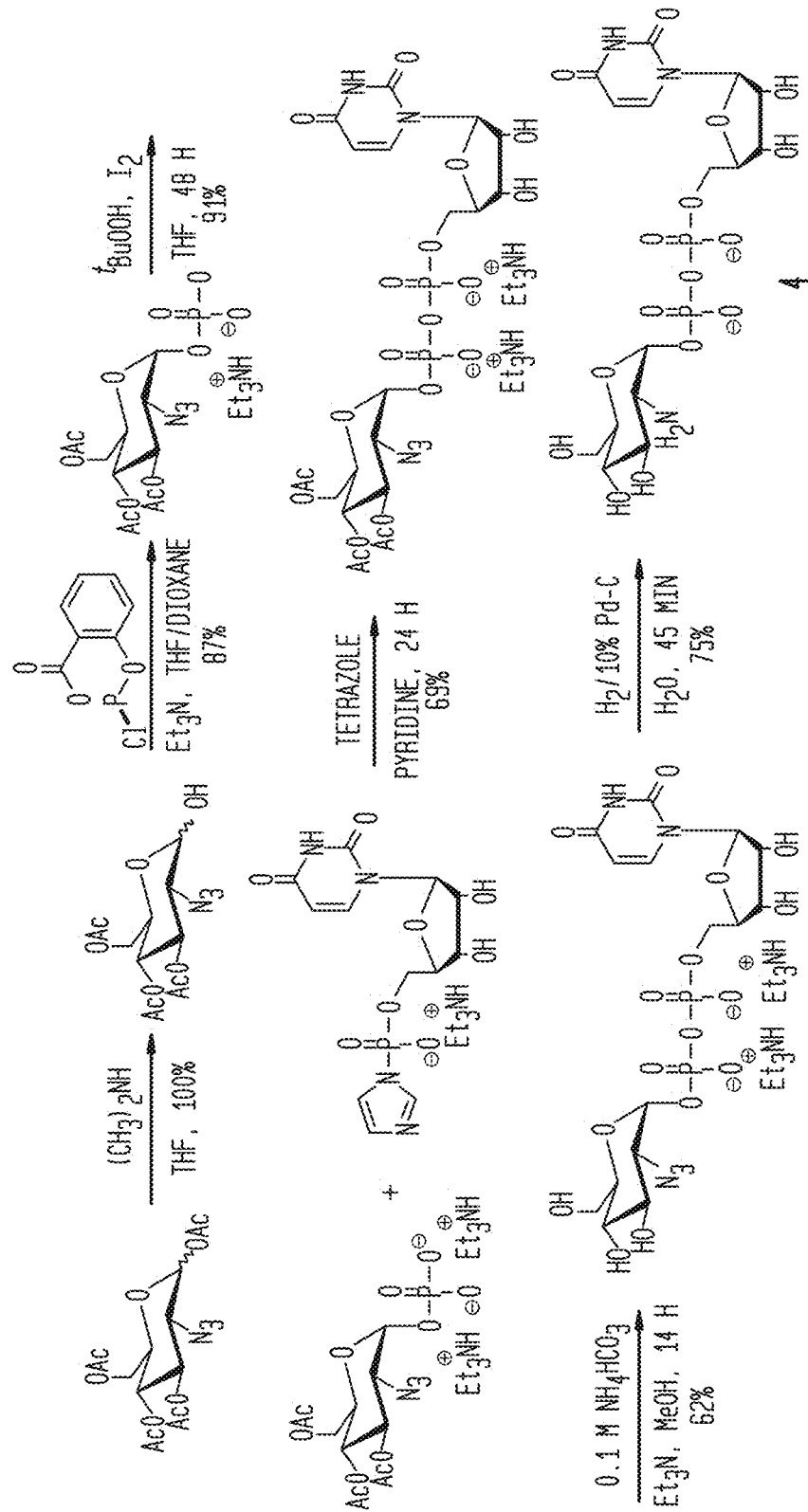

UDP-glucosamine cofactors UDP-6-GlcN 3 and UDP-2-GlcN 4 were synthesized by hydrogenation with $H_2$ on Pd/C from 1 and 2, respectively (FIG. 3) [Takaya, K., Nagahori, N., Kurogochi, M., Furuike, T., Miura, N., Monde, K., Lee, Y. C. and Nishimura, S. (2005) Rational design, synthesis, and characterization of novel inhibitors for human beta-1,4-galactosyltransferase. *J. Med. Chem.*, 48, 6054-6065]. UDP-2-Keto-Glc 5 was synthesized according to a previously reported method [Dulcey, A. E., Qasba, P. K., Lamb, J. and Griffiths, G. L. (2011) Improved synthesis of UDP-2-(2-ketopropyl)galactose and a first synthesis of UDP-2-(2-ketopropyl)glucose for the site-specific linking of biomolecules via modified glycan residues using glycosyltransferases. *Tetrahedron*, 67, 2013-2017; Boeggeman, E., Ramakrishnan, B. and Qasba, P. K. (2010), *Annual Conference of the Society for Glycobiology*, St Pete Beach, Fla., Vol. 20, pp. 1511]. The final products were purified with a Develosil RP Aqueous C30 semi-preparative column by HPLC, and their identities and purities were confirmed by LC-MS and high-resolution mass spectrometry.

Enzymatic Transfer of UDP-GlcN and UDP-Glc Derivatives to BGT DNA.

T4 phage α- and β-glucosyltransferases (AGT and BGT, respectively) specifically transfer the glucose moiety of UDP-Glc to 5-hmC residues in ds DNA, making α- and β-glucosyloxy-5-methylcytosine (5-gmC) [Tomaschewski, J., Gram, H., Crabb, J. W. and Ruger, W. (1985) T4-induced alpha- and beta-glucosyltransferase: cloning of the genes and a comparison of their products based on sequencing data. *Nucleic Acids Res.*, 13, 7551-7568; Szwagierczak, A., Bultmann, S., Schmidt, C. S., Spada, F. and Leonhardt, H. (2010) Sensitive enzymatic quantification of 5-hydroxymethylcytosine in genomic DNA. *Nucleic Acids Res.*, 38, e181]. The transfer efficiency of compounds 1-5 by AGT, BGT, and BGT/Y261L mutant [Boeggeman, E., Ramakrishnan, B. and Qasba, P. K. (2010), *Annual Conference of the Society for Glycobiology*, St Pete Beach, Fla., Vol. 20, pp. 1511] was assessed by incubating various concentrations of each compound with BGT DNA (FIGS. 4 and 5).

BGT DNA contains 5-hmC instead of cytosine and was produced from phage deficient in α- and β-glucosyltransferases. The degree of glycosylation of BGT DNA was determined by incubating the samples with the restriction endonuclease MfeI. Because MfeI cleaves $^{5-hm}C\downarrow$AATTG sites but is blocked by their glycosylation, this restriction enzyme was used to quantify the transfer efficiency of each of the UDP-GlcN and UDP-Glc derivatives by the glucosyltransferases.

Figure 4:
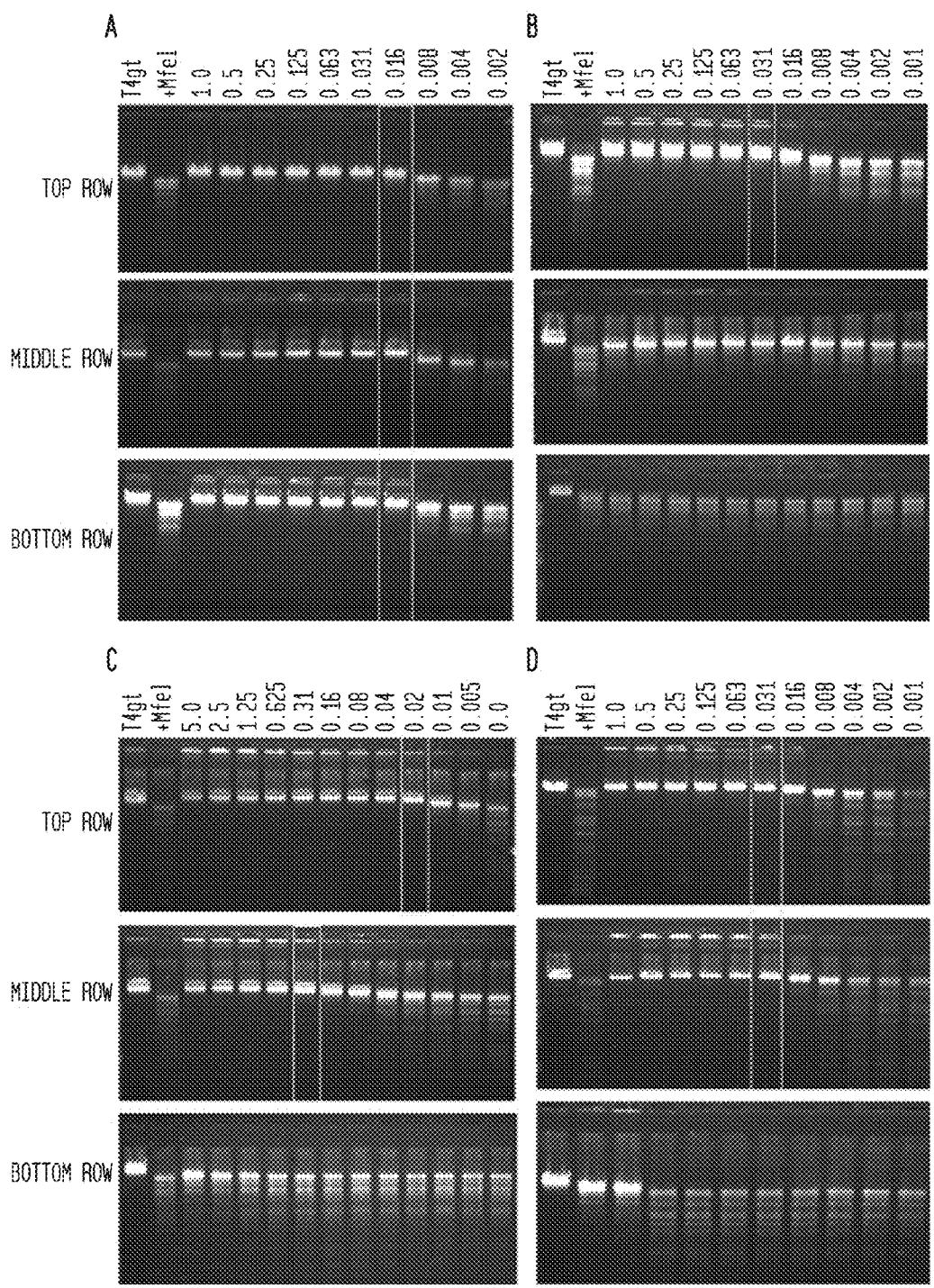
FIG. 4 shows images of agarose gels depicting the results of enzymatic transfer experiments with wild-type BGT (top row), BGT/Y261L (middle row), and wild-type AGT (bottom row) using UDP-Glc derivatives as substrates. (A) natural UDP-Glc, (B) UDP-6-Azido-Glc 1, (C) UDP-6-GlcN 3, and (D) UDP-2-GlcN 4.

FIG. 4 shows the results of enzymatic transfer experiments with (A) natural UDP-Glc, (B) UDP-6-Azido-Glc 1, (C) UDP-6-GlcN 3, and (D) UDP-2-GlcN 4. Top row: wild-type BGT; middle row: BGT/Y261L; bottom row: wild-type AGT. The vertical parallel lines show the minimum concentration for complete protection of BGT DNA against MfeI cleavage, which cuts hydroxymethylated cytosine (hmC) at $^{hm}$CAATTG. Various concentrations of UDP-Glc derivatives (as indicated) were incubated with 0.25 µg BGT DNA in the presence of 100 ng of glucosyltransferase at 37° C. for 1 hour. Then the glucosyltransferase was killed by heat at 70° C., and 1 µL (20 units) MfeI was added and incubated at 37° C. for 1 hour. The results were analyzed by agarose gel electrophoresis. Concentration values are given in mM.

Figure 5:
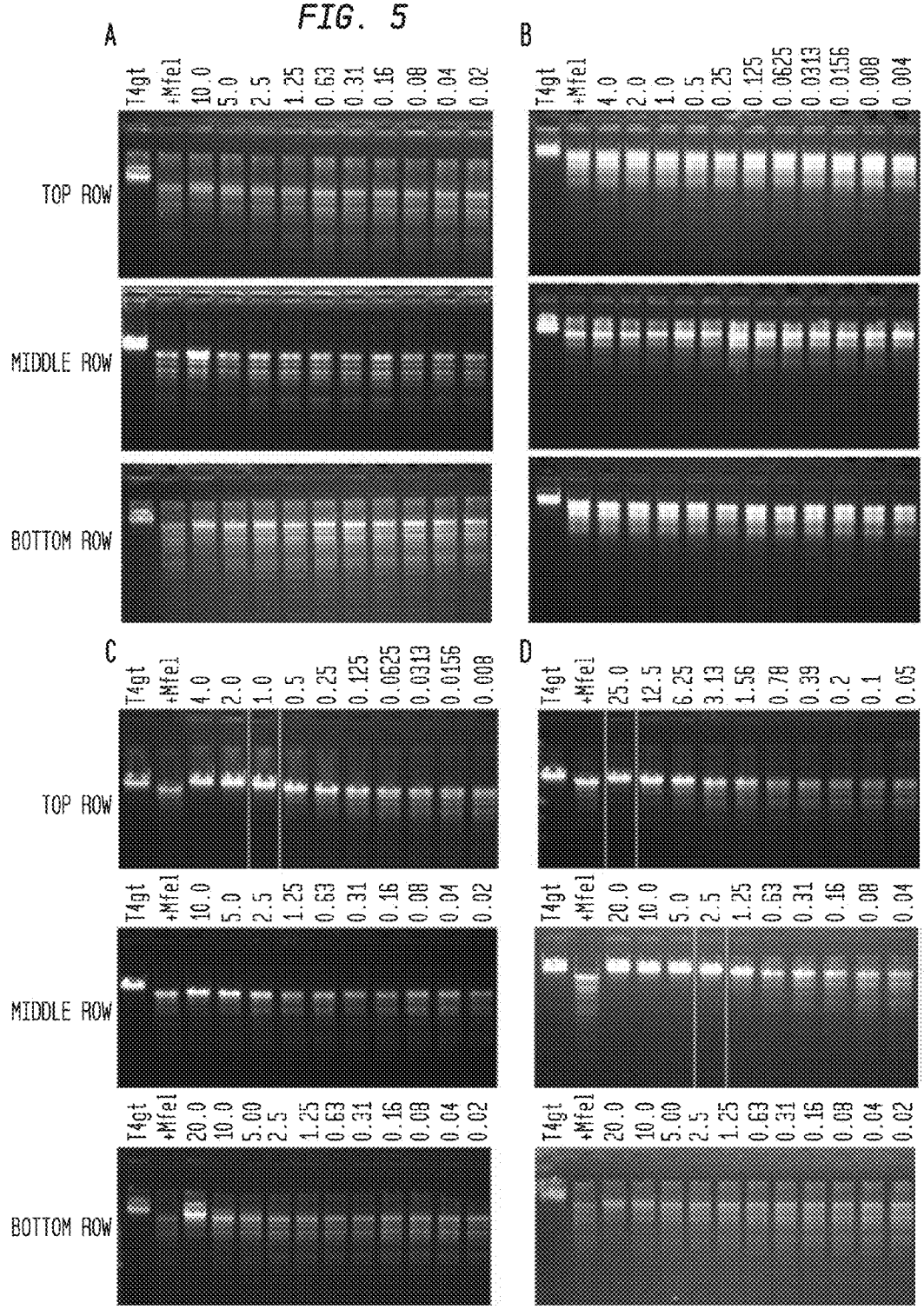
FIG. 5 shows images of agarose gels depicting the results of enzymatic transfer experiments with wild-type BGT (top row), BGT/Y261L (middle row), and wild-type AGT (bottom row) using UDP-Glc derivatives as substrates. UDP-2-Azido-Glc 2 (A), UDP-2-Keto-Glc 5 (B), UDP-GlcUA (C), and UDP-GlcNAc (D).

FIG. 5 shows the results of enzymatic transfer experiments with (A) UDP-2-Azido-Glc 2, (B) UDP-2-Keto-Glc 5, (C) UDP-GlcUA, and (D) UDP-GlcNAc. Top row: wild-type BGT; middle row: BGT/Y261L; bottom row: wild-type AGT. The vertical parallel lines show the minimum concentration for complete protection of BGT DNA against MfeI cleavage, which cuts hmC at $^{hm}$CAATTG. Various concentrations of each substrate (as indicated) were incubated with 0.25 μg BGT DNA in the presence of 100 ng glucosyltransferase at 37° C. for 1 hour. Then the glucosyltransferase was killed by heat at 70° C. for 10 minutes, and 1 μL (20 units) MfeI was added and incubated at 37° C. for 1 hour. The results were analyzed by agarose gel electrophoresis. Concentration values are given in mM.

Figure 6:
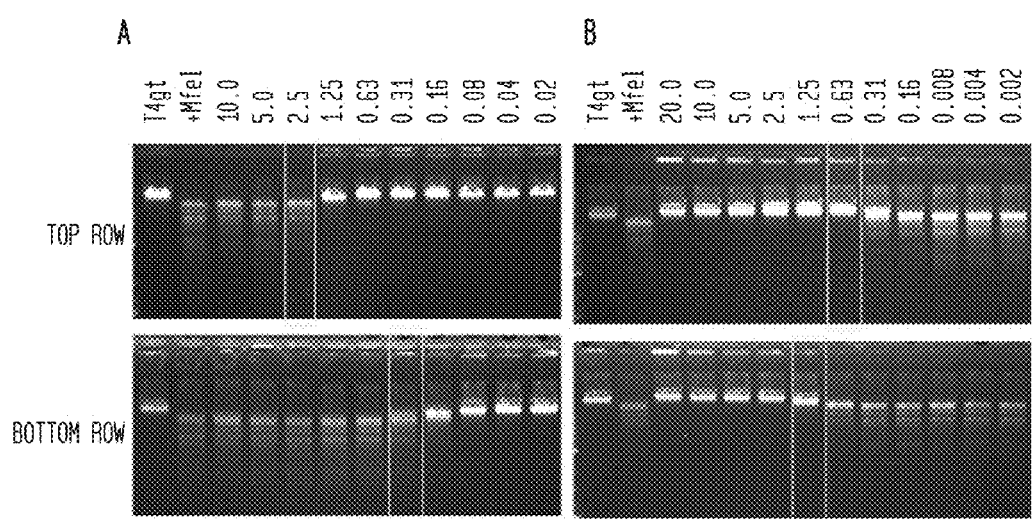
FIG. 6 shows images of agarose gels depicting the results of UDP-2-Azido-Glc 2 inhibitory tests with wild-type BGT (top row) and BGT/Y261L (bottom row).

FIG. 6 shows the results of UDP-2-Azido-Glc 2 inhibitory tests with wild-type BGT (top row) and BGT/Y261L (bottom row). FIG. 6A: Various concentrations of UDP-2-Azido-Glc 2 (as indicated) in the presence of 40 μM underivatized UDP-Glc. The vertical parallel lines indicate the minimum concentration of UDP-2-Azido-Glc 2 in which BGT DNA is not protected against MfeI cleavage, demonstrating that the glucose transfer is inhibited. FIG. 6B: Various concentrations of natural UDP-Glc (as indicated) in the presence of 5 mM UDP-2-Azido-Glc 2. The vertical parallel lines indicate the minimum concentration of UDP-2-Azido-Glc 2 for complete protection of BGT DNA against MfeI cleavage. Concentration values are given in mM. The results show that UDP-2-Azido-Glc 2 is a competitive inhibitor for wild-type BGT and BGT/Y261L.

UDP-6-Azido-Glc 1, UDP-6-GlcN 3, and UDP-2-GlcN 4 were transferred by wild-type BGT with similar efficiency as the natural UDP-Glc (FIG. 4). None of the synthesized UDP-GlcN or UDP-Glc derivatives could be efficiently transferred by wild-type AGT. AGT and BGT proteins share about 20% sequence similarity, but differ in the formation of the glycosidic linkage: AGT is a retaining, whereas BGT is an inverting glycosyltransferase.

BGT can glycosylate all available 5-hmC bases in acceptor DNA; however, AGT has some restrictions and its precise substrate specificity is not yet fully understood [Tomaschewski, J., Gram, H., Crabb, J. W. and Ruger, W. (1985) T4-induced alpha- and beta-glucosyltransferase: cloning of the genes and a comparison of their products based on sequencing data. *Nucleic Acids Res.*, 13, 7551-7568]. Interestingly, the mutant BGT/Y261L transferred UDP-2-GlcN 4 with similar efficiency as natural UDP-Glc, but the transfer efficiency for UDP-6-GlcN 3 was about 15-fold lower. According to Qasba et al., the side chain of Tyr261 hinders the binding of the N-acetyl-group of UDP-GlcNAc allowing only UDP-Glc to be the donor substrate; consequently, the Y261L mutation enhances the enzyme activity towards GlcNAc or glucose with a chemical tag at the C2 position [Boeggeman, E., Ramakrishnan, B. and Qasba, P. K. (2010), *Annual Conference of the Society for Glycobiology*, St Pete Beach, Fla., Vol. 20, pp. 1511]. In fact, it was observed that BGT/Y261L transfers UDP-GlcNAc 10-fold more efficiently than the wild-type BGT (FIG. 5). However, compared to UDP-2-GlcN 4, which lacks the N-acetyl-group, the transfer efficiency of UDP-GlcNAc by the Y261L enzyme is approximately 100-fold lower. Furthermore, the transfer of UDP-2-Keto-Glc 5 by BGT/Y261L was not detected at the highest tested concentration (4 mM).

None of the three tested enzymes efficiently transferred UDP-2-Azido-Glc 2 to 5-hmC residues in BGT DNA (FIG. 5). UDP-2-Azido-Glc acts as a competitive inhibitor for wild-type BGT and BGT/Y261L (FIG. 6A), but not for AGT. Likewise, with the increase of natural UDP-Glc concentration, UDP-2-Azido-Glc could be chased out to restore the activity of the β-glucosyltransferase (FIG. 6B). The transfer efficiencies of the synthesized UDP-Glc derivatives 1-5, along with the native UDP-Glc cofactor and the commercially available UDP-sugars, UDP-Glucuronic acid (UDP-GlcUA) and UDP-N-acetyl-D-glucosamine (UDP-GlcNAc), are presented in Table 1.

TABLE 1

UDP-Sugar concentration required for complete protection of BGT DNA from MfeI cleavage.

| Enzyme | Concentration of UDP-Sugar (mM) | | | | | | | |
|---|---|---|---|---|---|---|---|---|
| | UDP-Glc | UDP-GlcUA | UDP-GlcNAc | 1 | 2 | 3 | 4 | 5 |
| BGT | 0.02 | 1.0 | 25 | 0.04 | n.a. | 0.02 | 0.03 | >>4.0 |
| BGT/Y261L | 0.02 | >>10.0 | 2.5 | >>1.0 | n.a. | 0.31 | 0.03 | >>4.0 |
| AGT | 0.02 | >>20.0 | >>20.0 | n.a. | n.a. | >>5.0 | >>1.25 | n.a. |

>>incomplete protection event at the highest tested concentration; n.a.: no activity; UDP-Glc: UDP-Glucose; UDP-GlcUA: UDP-Glucuronic acid; UDP-GlcNAc: UDP-N-acetyl-D-glucosamine; 1: UDP-6-Azido-Glc; 2: UDP-2-Azido-Glc; 3: UDP-6-glucosamine, UDP-6-GlcN; 4: UDP-2-glucosamine, UDP-2-GlcN; 5: UDP-2-Keto-Glc.

Without wishing to be bound by any theory, the size and polarity of the group at the O2' position may be comparatively more important for the catalytic activity of BGT. Site-specific mutations around the O6' binding area may enable mutant BGT enzymes to transfer larger molecules, such as UDP-GlcN or UDP-Glc derivatives with covalently bound reporter groups such as fluorophores or biotin.

It is surprising that BGT/Y261L cannot efficiently transfer UDP-6-Azido-Glc. Without wishing to be bound by any theory, it is believed that the concurrent polarity change at the O2' and O6' positions may result in the structural alterations of the enzyme binding pocket, which may cause inactivation of the enzyme.

Fluorescent Labeling of Glucosamine-Modified Oligonucleotides.

Next, the labeling of 2- and 6-glucosamine-modified 5-hmC residues with commercially available fluorescent probes was investigated, and the results with the 6-azido-glucose DNA template were compared. To this end, a synthetic 49-mer 5'-FAM-labeled duplex oligonucleotide containing a single 5-hmC residue [Kinney, S. M., Chin, N. G., Vaisvila, R., Bitinaite, J., Zheng, Y., Esteve, P. O., Feng, S., Stroud, H., Jacobsen, S. E. and Pradhan, S. (2011) Tissue-specific distribution and dynamic changes of 5-hydroxymethylcytosine in mammalian genomes. *J Bio Chem*, 286, 24685-24693] was first incubated with wild-type BGT and the compounds UDP-6-Azido-Glc 1, UDP-6-GlcN 3, or UDP-2-

GlcN 4, to generate the corresponding 6-azido-glucosyloxymethylcytosine, 6-glucosaminyloxymethylcytosine and 2-glucosaminyloxymethylcytosine oligonucleotides. After purification by phenol extraction followed by ethanol precipitation, the azido-glucose- and glucosamine-containing oligonucleotides were chemically labeled with an orthogonal fluorescent probe via click chemistry (for 1) or activated ester coupling (for 3 and 4) (FIG. 7).

Figure 7:
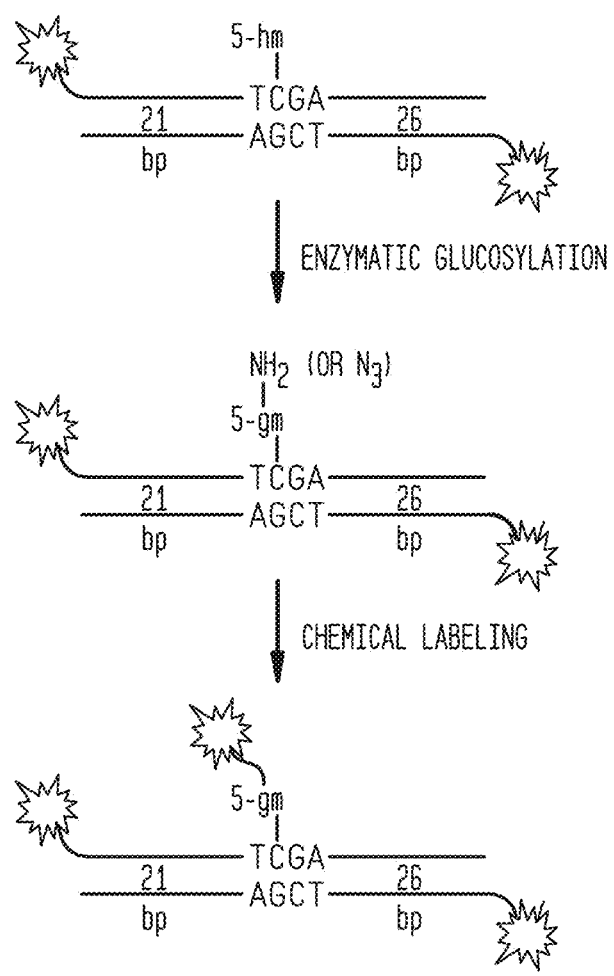
FIG. 7 shows a schematic of an assay for identifying hmC in DNA.

FIG. 7 shows a schematic for the two-step detection of 5-hmC residues in a 5'-FAM-labeled duplex oligonucleotide with reporter probes: (1) BGT mediated transglycosylation reaction using UDP-glucosamine or UDP-glucose and (2) Chemical labeling of resulting glucosamine- or azido-sugar-containing duplex oligonucleotide with fluorescent probes. TaqI restriction endonuclease cleaves the sequence T↓CGA at the position indicated by the arrow.

Figure 8:
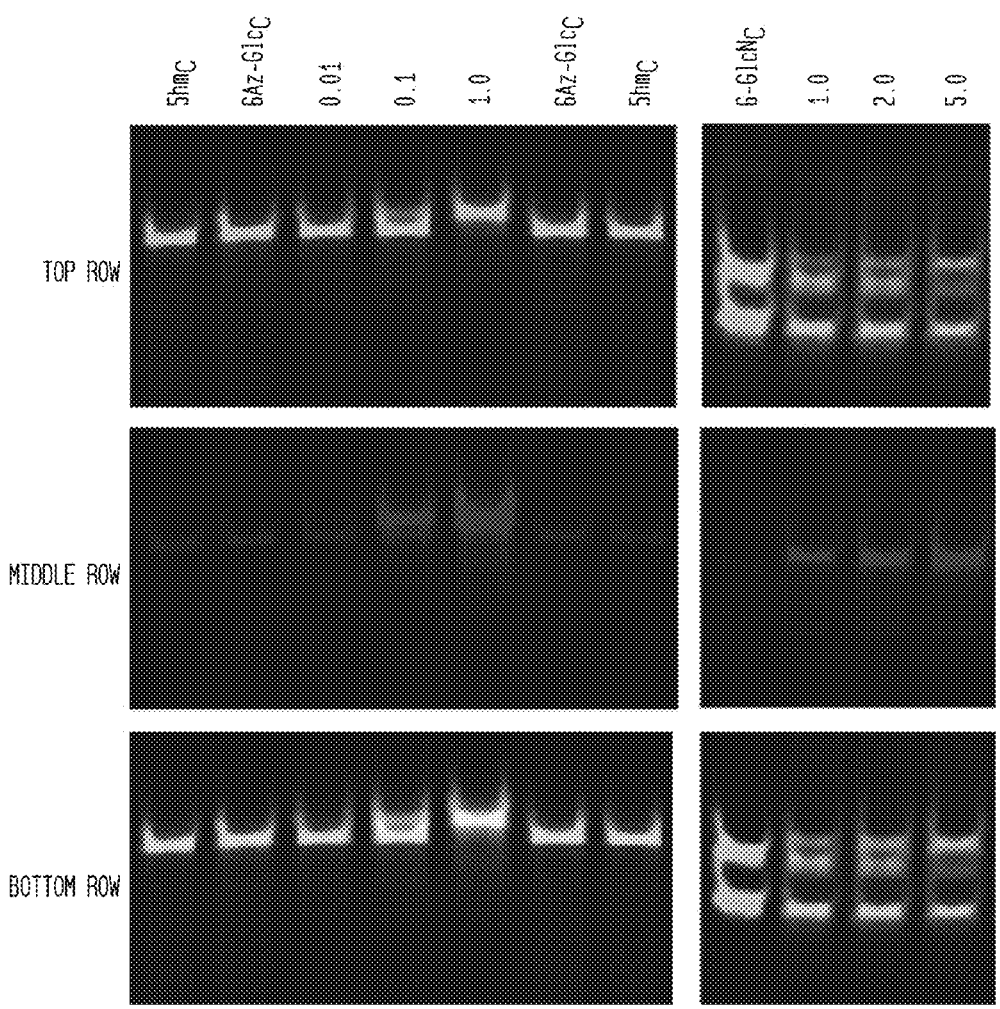
FIG. 8 shows images agarose gels depicting the results of labeling tests of (A) 6-Azido-Glc- and (B) 6-glucosamine-containing synthetic oligonucleotides.

For the click chemistry coupling, 6-Azido-Glc-modified oligonucleotide (5 µM) was incubated with 0.01 to 1.0 mM of dibenzylcyclooctyne-tetramethylrhodamine (DBCO-Fluor 545) at room temperature for 18 hours. For the activated ester coupling, 2- or 6-glucosamine-modified oligonucleotides (5 µM) were incubated with various concentrations of TAMRA NHS ester, ranging from 1.0 mM to 5.0 mM, in 20 mM phosphate buffer pH 6.8 at room temperature for 18 hours. The coupling efficiency of each coupling reaction was analyzed using a scanning fluorometer after electrophoretic separation of products on a 10-20% acrylamide gel (FIG. 8). To allow a better distinction between labeled and unlabeled bands, samples were digested with TaqI restriction endonuclease (FIG. 9). Because the cyclooctyne-based linker led to a substantial band shift, the click chemistry coupling reactions could be directly visualized on gel without the need for restriction digestion.

FIG. 8 shows the results of labeling tests of (A) 6-Azido-Glc- and (B) 6-GlcN-containing synthetic oligonucleotides. For copper-free click coupling, 50 pmols FAM-labeled 49-bp synthetic oligonucleotide containing a single 6-Azido-Glc were incubated with the indicated concentrations of DBCO-Fluor 545 (in mM) at room temperature for 18 hours. For NHS-ester coupling, 50 pmols FAM-labeled 49-bp synthetic oligonucleotide containing a single 6-glucosamine were incubated with the indicated concentrations of TAMRA NHS ester (in mM) in 20 mM phosphate buffer pH 6.8 at room temperature for 18 hours, and subsequently cleaved with 1 µL (20 units) TaqI restriction endonuclease for 1 hour at 37° C. in order to separate labeled from unlabeled oligonucleotides. Top row: FAM channel (488 nm); middle row: TAMRA channel (532 nm); bottom row: overlay.

FIG. 9 shows the results of restriction endonuclease cleavage of 5-hmC- and 5-gmC-containing oligonucleotides. FAM-labeled 49-bp synthetic oligonucleotide (1 nmol) was glycosylated with 100 ng of BGT for 18 hours at 37° C. in a total 100 mL reaction containing 50 mM HEPES buffer pH 7.6, 10 mM MgCl$_2$, 50 mM NaCl supplemented with 0.5 mM UDP-6-GlcN. Aliquots (10 pmol) were digested for 1 hour at 37° C. either with 1 µL (20 units) of XhoI or TaqI before (lanes 1-3) and after (lanes 4-6) glycosylation. XhoI restriction endonuclease cleaves CT5-$^{hm}$CGAC sites, but is blocked by 5-$^{hm}$C glycosylation. TaqI cleaves both T5-$^{hm}$CGA and T5-$^{gm}$CGA sites.

Figure 10:
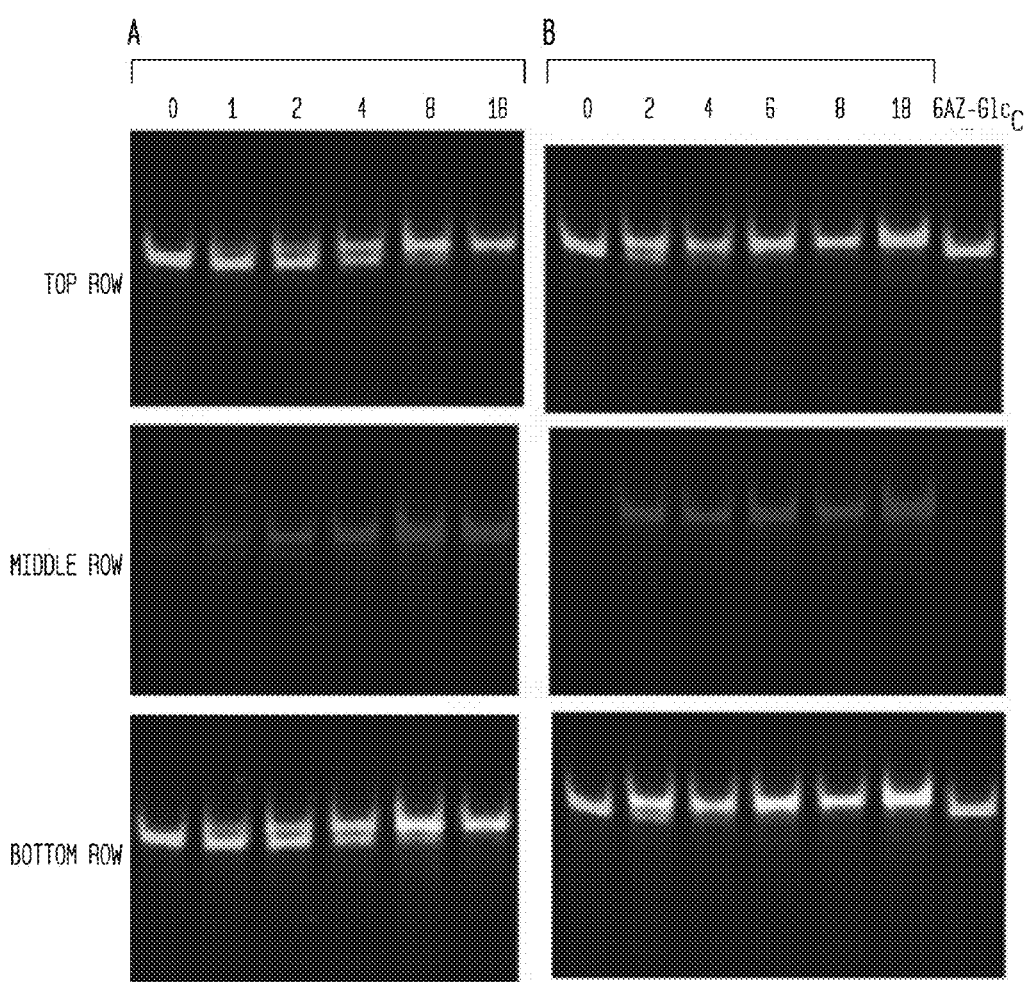
FIG. 10 shows images of agarose gels depicting the results of labeling of a 6-Azido-Glc-modified oligonucleotide at different temperatures.

FIG. 10 shows the results of labeling of a 6-Azido-Glc-modified oligonucleotide at different temperatures. FAM-labeled 49-bp synthetic oligonucleotide (50 pmols) containing a single 6-Azido-Glc was incubated with 1 mM DBCO-Fluor 545 for 0, 2, 4, 8 and 18 h at (A) room temperature or (B) at 37° C. Top row: FAM channel (488 nm); middle row: TAMRA channel (532 nm); bottom row: overlay.

Figure 11:
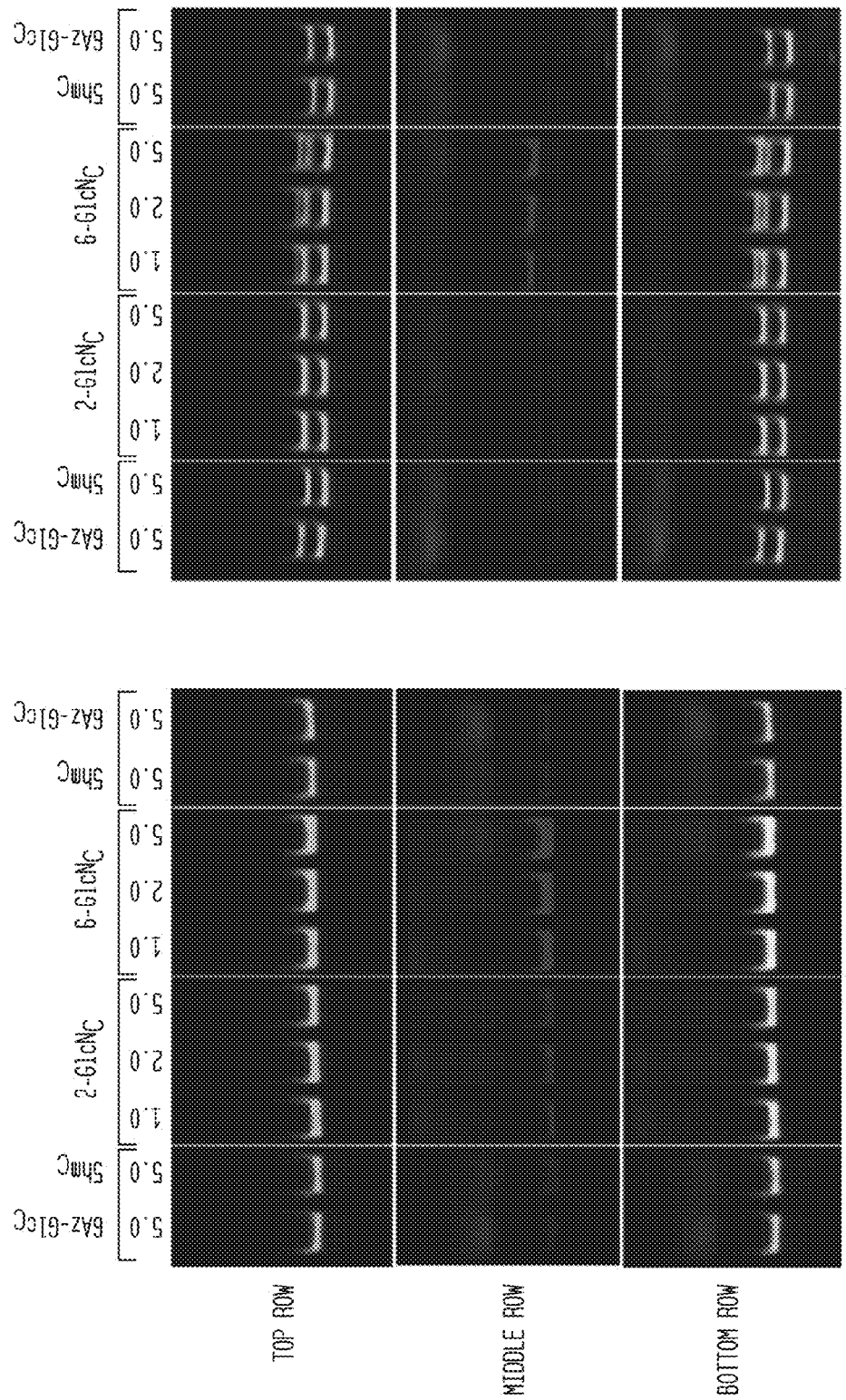
FIG. 11 shows images of agarose gels depicting the results of labeling of 6-glucosamine- and 2-glucosamine-modified oligonucleotides.

FIG. 11 shows the results of labeling of 6-glucosamine- and 2-glucosamine-modified oligonucleotides. FAM-labeled 49-bp synthetic oligonucleotide (50 pmols) containing either a single 6-glucosamine or a 2-glucosamine were incubated with different concentrations of TAMRA NHS ester (as indicated) in HEPES buffer pH 7.6 at room temperature for 18 hours. Top row: FAM channel (488 nm); middle row: TAMRA channel (532 nm); bottom row: overlay. Concentration values are given in mM. (A) Uncut oligonucleotides; (B) Oligonucleotides cleaved by TaqI. TaqI treatment generates two smaller ds oligonucleotides and allows for a clearer distinction among labeled and unlabeled 5-gmC residues. Labeling efficiencies were estimated at the FAM channel by comparing fluorescence intensity from cut oligonucleotide bands.

Figure 12:
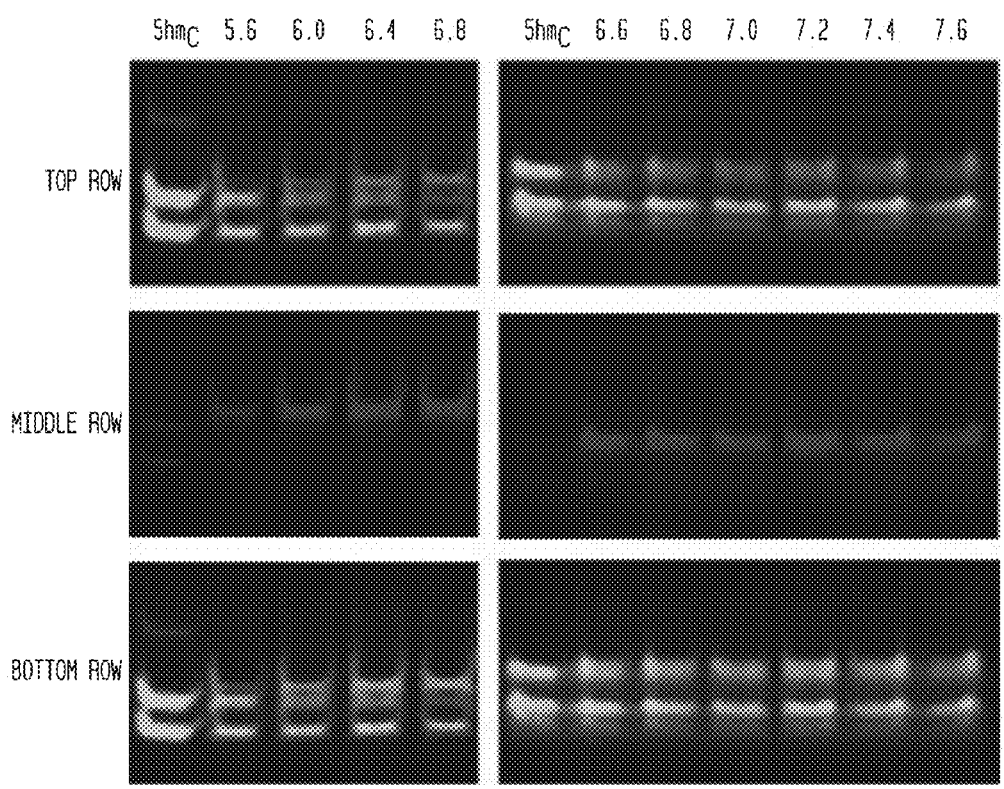
FIG. 12 shows images of agarose gels depicting the results of labeling of 6-glucosamine-modified oligonucleotides at different pHs.

FIG. 12 shows the results of labeling of 6-glucosamine-modified oligonucleotides at different pHs. FAM-labeled 49-bp synthetic oligonucleotide (50 pmols) containing a single 6-glucosamine were incubated with 5.0 mM TAMRA NHS ester in 20 mM phosphate buffer with pHs ranging from 5.6-7.6 at room temperature for 18 hours. The resulting oligonucleotides were cleaved with TaqI before gel electrophoresis. Top row: FAM channel (488 nm); middle row: TAMRA channel (532 nm); bottom row: overlay. The results show that the best pH range for NHS ester labeling is between pH 6.8-7.4.

Figure 13:
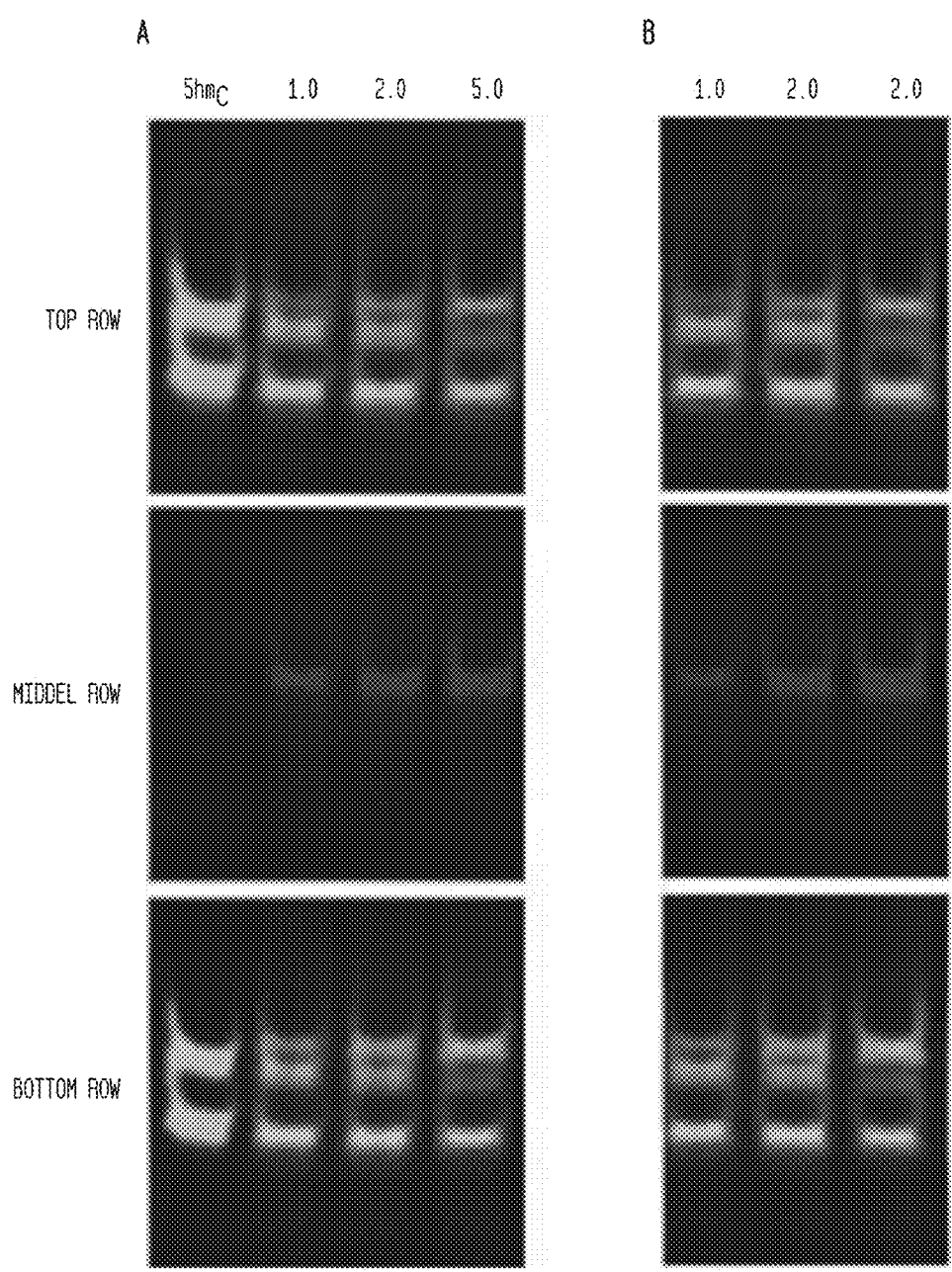
FIG. 13 shows images of agarose gels depicting the results of labeling of 6-glucosamine-modified oligonucleotides at different temperatures.

FIG. 13 shows the results of labeling of 6-glucosamine-modified oligonucleotides at different temperatures. Various concentrations of FAM-labeled 49-bp synthetic oligonucleotide containing a single 6-glucosamine (as indicated) were incubated with 5.0 mM TAMRA NHS ester in 20 mM pH 6.8 phosphate buffer for 18 hours at (A) room temperature or (B) 37° C. The resulting oligonucleotides were cleaved with TaqI before gel electrophoresis. Top row: FAM channel (488 nm); middle row: TAMRA channel (532 nm); bottom row: overlay. Concentration values are given in mM. The results show that increasing temperature doesn't significantly affect the NHS ester labeling efficiency.

The results show that for the click coupling, 1 mM DBCO-Fluor 545 was sufficient to label 5 µM single 6-Azido-Glc-modified oligonucleotide within 18 hours at room temperature (FIG. 8A) or 8 hours at 37° C. (FIG. 10) with close to 100% labeling yield. For the activated ester method, 5 mM TAMRA NHS ester was required to efficiently label 5 µM single 6-glucosamine-modified oligonucleotide within 18 h at room temperature at the optimized pH of 6.8 (FIGS. 8B, 11, 12, and 13). The labeling ratio for TAMRA NHS coupling with the 6-glucosamine-modified oligonucleotide ranged from 80%-90%.

Labeling DNA with glucosamine offers some unique advantages. For example, by combination of commercially available anti-glucosamine antibodies and amine-reactive fluorogenic tags, such as naphthalene-2,3-dicarboxaldehyde (NDA) and fluorescamine [Wang, W., Maniar, M., Jain, R., Jacobs, J., Trias, J. and Yuan, Z. (2001) A fluorescence-based homogeneous assay for measuring activity of UDP-3-O—(R-3-hydroxymyristoyl)-N-acetylglucosamine deacetylase. *Anal Biochem*, 290, 338-346; Skelley, A. M. and Mathies, R. A. (2006) Rapid on-column analysis of glucosamine and its mutarotation by microchip capillary electrophoresis. *J Chromatogr A*, 1132, 304-309; Novatchev, N. and Holzgrabe, U. (2002) Evaluation of amino sugar, low molecular peptide and amino acid impurities of biotechnologically produced amino acids by means of CE. *J Pharm Biomed Anal*, 28, 475-486], 5-hmC enrichment and identification methods can be developed and may find practical application in epigenetic research. Furthermore, the chemical orthogonality of the azido and amino labeling systems opens up the possibility to simultaneously label 5-hmC residues with different synthetic probes using engineered glycosyltransferases capable of selectively transferring either a glucosamine or an azido-modified glucose moiety.

In summary, a new method for labeling 5-hmC residues in duplex DNA with fluorescent or affinity probes has been described. In some embodiments, the method involves using a UDP-GlcN cofactor, where small amino groups are amenable for indirect labeling, and transferring these glucosamine moieties using the transglycosylation reaction mediated by T4 phage glucosyltransferases. The labeling of glucosamine-containing DNA can optionally be achieved using activated NHS-esters to install the desired reporter group on DNA for downstream applications, such as locus-specific detection 5-hmC or selective enrichment of 5-hmC by standard affinity purification protocols. Equipping 5-hmC residues in DNA molecules with reporter probes can elucidate not only the 5-hmC distribution in the genome, but also its temporal fluctuation and maintenance, both in healthy and diseased states, as well as how it is influenced by local environment changes and the biology of each individual.

Example 2

Synthesis of UDP-GlcN and UDP-Glc Derivatives

Materials

Reagents were purchased from Sigma-Aldrich; solvents were purchased from Fisher unless otherwise noted. Anhydrous solvents were purchased from ACROS, and used directly from sealed bottles, which were stored under argon. Brine (NaCl), NaHCO$_3$, and NH$_4$Cl refer to saturated aqueous solutions unless otherwise noted. Silica column chromatography was performed with 32-63 µm silica gel and reagent grade solvents. Analytical LC-MS was performed on a Waters X-Bridge C18 reverse phase column (2.5 µm, 4.6×75 mm) or a Develosil C30 RP Aqueous reverse phase column (5 µm, 4.6×150 mm) with H$_2$O and CH$_3$CN as mobile phases on an Agilent 1200 HPLC system equipped with Agilent 6120 Quadrupole Mass Detector at both positive and negative mode. Preparative HPLC purification was performed on a Waters X-Bridge C18 reverse phase column (5 µm, 10×150 mm) or a Develosil RP Aquesous C30 column (5 µm, 10×150 mm) with 100 mM pH 7.0 TEAB and CH3CN as mobile phases on an Agilent 1200 HPLC system, unless otherwise noted. UV gel pictures were taken on an AlphaImager HP gel imaging system. Fluorescence gel pictures were taken on a GE Health Care Typhoon 9400 high performance gel and blot imager at 488 nm (FAM, green false color) or 532 nm (TAMRA, red false color).

Methods

Synthesis of UDP-6-Azido-Glc (FIG. 2B; compound 1) and UDP-2-Azido-Glc (FIG. 2B; compound 2)

UDP-6-Azido-Glc 1 and UDP-2-Azido-Glc 2 were synthesized from 6-Azido-6-deoxy-D-glucose (Carbosynth #MA02620, Compton, Berkshire, UK) and 1,3,4,6-Tetra-O-acetyl-2-azido-2-deoxy-β-D-glucopyranose (TCI America, # T2196, Portland, Oreg.), respectively, according to published methods [Marchesan, S, and Macmillan, D. (2008) Chemoenzymatic synthesis of GDP-azidodeoxymannoses: non-radioactive probes for mannosyltransferase activity. *Chem. Commun.*, 4321-4323; Song, C. X., Szulwach, K. E., Fu, Y., Dai, Q., Yi, C., L1, X., Li, Y., Chen, C. H., Zhang, W., Jian, X. et al. (2011) Selective chemical labeling reveals the genome-wide distribution of 5-hydroxymethylcytosine. *Nat. Biotechnol.*, 29, 68-72] and their identities and purities were confirmed by HRMS, and analytical HPLC, respectively. UDP-6-Azido-Glc 1: HRMS (m/z): [M-H]-calculated for $C_{15}H_{22}N_5O_{16}P_2$, 590.0542; observed, 590.0545. UDP-2-Azido-Glc 2: HRMS (m/z): [M-H]-calculated for $C_{15}H_{22}N_5O_{16}P_2$, 590.0542; observed, 590.0548.

Synthesis of UDP-6-GlcN (FIG. 2B; compound 3).

UDP-6-Azido-Glc 1 (37 mg, 0.062 mmol) was dissolved in 15 mL H$_2$O, and 10% Pd—C (40 mg) was added. The reaction mixture was stirred under 1 atm H2 at room temperature for 45 minutes. Then the resulting solution was filtered through 0.22 µm membrane, concentrated by lyophilization, and then purified with HPLC on a Develosil C30 RP Aqueous reverse phase column. The final product was obtained as a white solid (30 mg, 85%). HRMS (m/z): [M-H]-calculated for $C_{15}H_{24}N_3O_{16}P_2$, 564.0637; observed, 564.0641.

Synthesis of UDP-2-GlcN (FIG. 2B; Compound 4).

UDP-2-Azido-Glc 2 (17 mg, 0.027 mmol) was dissolved in 8 mL H2O, and 10% Pd—C (25 mg) was added. The reaction mixture was stirred under 1 atm H2 at room temperature for 45 min. Then the resulting solution was filtered through 0.22 µm membrane, concentrated by lyophilization, and then purified with HPLC on a Develosil C30 RP Aqueous reverse phase column. The final product was obtained as a white solid (12 mg, 74%). HRMS (m/z): [M-H]-calculated for $C_{15}H_{24}N_3O_{16}P_2$, 564.0637; observed, 564.0634.

Synthesis of UDP-2-Keto-Glc (FIG. 2B; Compound 5).

UDP-2-Keto-Glc 5 was synthesized according to a published protocol [Dulcey, A. E., Qasba, P. K., Lamb, J. and Griffiths, G. L. (2011) Improved synthesis of UDP-2-(2-ketopropyl)galactose and a first synthesis of UDP-2-(2-ketopropyl)glucose for the site-specific linking of biomolecules via modified glycan residues using glycosyltransferases. *Tetrahedron*, 67, 2013-2017], and its identity and purity were confirmed by HRMS, and analytical HPLC, respectively. HRMS (m/z): [M-H]-calculated for $C_{18}H_{27}N_2O_{17}P_2$, 605.0790; observed, 605.0776.

Example 3

Binding of Anti-Glucosamine (Anti-GlcN) Antibody to DNA Modified with Glucosamine Derivatives Antibody assays were performed with commercially available anti-D-glucosamine antibody (Abcam, #ab62666). Results indicated that anti-D-glucosamine antibody does not bind to C or 5-mC containing PCR T42K DNAs. For 5-hmC containing PCR T42K DNA treated with UDP-Glc, UDP-2-GlcN, UDP-6-GlcN, or UDP-6-Azido-Glc in the presence of BGT, only 2-GlcN-containing DNA showed significant binding by the anti-D-glucosamine antibody. Anti-D-glucosamine antibody did not bind to 5-hmC PCR T42K DNA containing 6-GlcN, 6-Azido-Glc or Glc.

Figure 14:
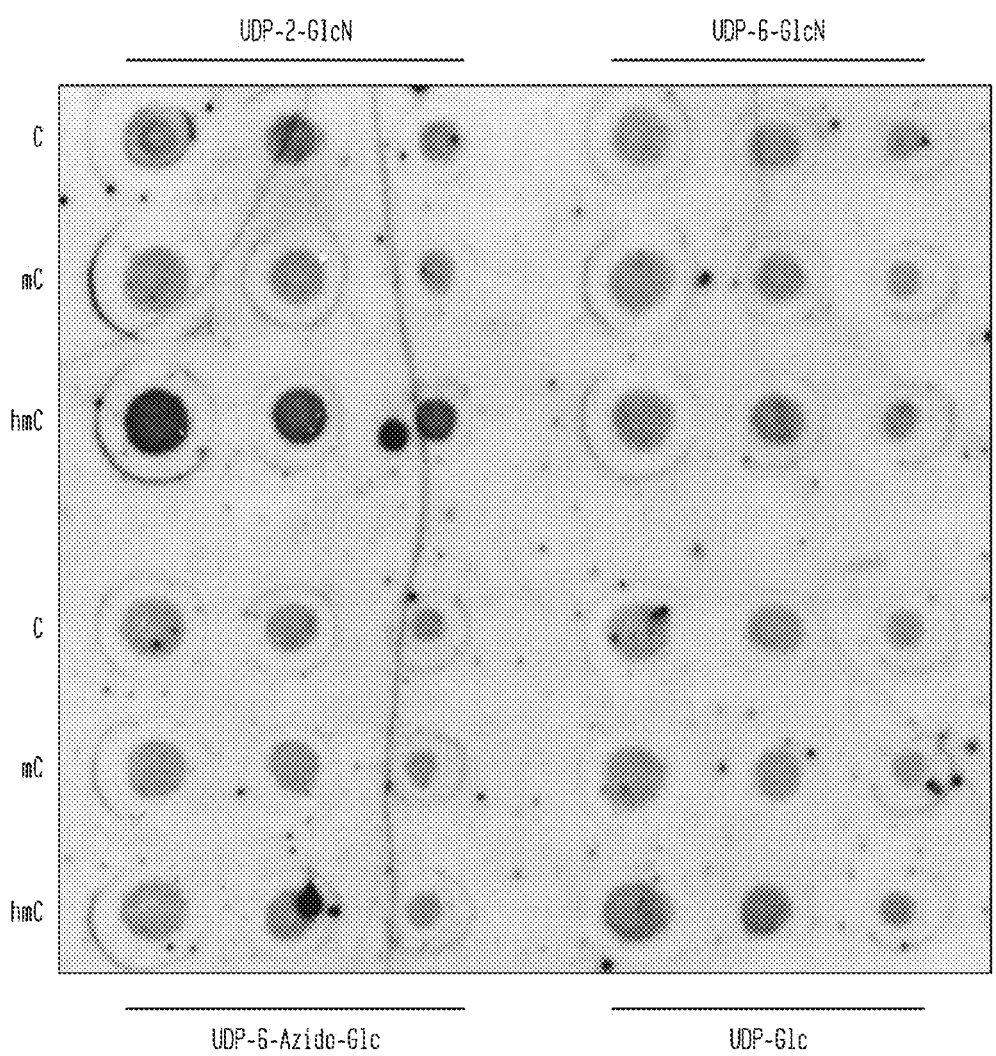
FIG. 14 shows an image depicting the results of an anti-D-glucosamine binding assay.

FIG. 14 shows the results of the anti-D-glucosamine binding assay. The assay was performed as follows: 400 ng of C, 5-mC, or 5-hmC PCR T42K DNA was treated with BGT and UDP-2-glucosamine, UDP-6-glucosamine, UDP-6-Azido-Glc, or natural UDP-Glc, respectively, for 1 h at 37° C. and then purified with QIA column. After measuring the O. D., DNA was diluted to proper concentration as desired. In this experiment, different amounts of DNA (for each part, first column: 150 ng, second column: 100 ng, third column: 50 ng) were denatured at 98° C. and spotted on a positively charged nylon membrane (Roche, #11209299001). UV crosslinking (3 min on a transilluminator) or chemical crosslinking was used to covalently attach the DNA to the membrane. The membrane was blocked in 5% milk (1×PBS, 0.1% Tween) for 1 hour and then anti-D-glucosamine antibody (Abcam, #ab62666) was added. The membrane was incubated at 4° C. for overnight and washed 3 times with 1×PBST buffer. The membrane was incubated with the secondary antibody, HRP-anti-rabbit IgG, for 1 hour, washed 3 times with 1×PBST buffer, and exposed to X-Film.

What is claimed is:

1. A cell free composition comprising:
   an isolated DNA β-glucosyltransferase;
   UDP-glucosamine (UDP-GlcN); and
   a restriction enzyme capable of cleaving a nucleic acid at a site comprising β-glucosyl-5-hydroxymethylcytosine but not a site comprising β-2-glucosaminyl-5-hydroxymethylcytosine.

2. The composition of claim 1, further comprising a buffer having a pH between 6 and 8.

3. The composition of claim 2, wherein the pH is between 6.8 and 7.4.

4. A cell free kit comprising:
   a DNA β-glucosyltransferase;
   UDP-GlcN; and
   a restriction enzyme capable of cleaving a nucleic acid at a site comprising β-glucosyl-5-hydroxymethylcytosine but not a site comprising β-2-glucosaminyl-5-hydroxymethylcytosine.

5. A method for labeling a modified nucleotide in a nucleic acid, comprising:
   (a) combining:
      i. a nucleic acid having a modified nucleotide
      ii. an isolated DNA β-glucosyltransferase; and
      iii. UDP-glucosamine (UDP-GlcN), to produce a mixture; and
   (b) incubating the mixture under conditions permitting the glucosamine to become covalently attached to the modified nucleotide in the nucleic acid; and
   (c) adding to the mixture:
      iv. a restriction enzyme capable of cleaving a nucleic acid at a site comprising β-glucosyl-5-hydroxymethylcytosine but not a site comprising β-2-glucosaminyl-5-hydroxymethylcytosine.

6. The method according to claim 5, wherein the modified nucleotide is hydroxymethylated cytosine (hmC).

7. The method according to claim 6, further comprising enriching, detecting, isolating and/or identifying the position of the glucosamine-attached nucleotide in the nucleic acid.

* * * * *